US012708468B2

(12) United States Patent
Malanowski

(10) Patent No.: US 12,708,468 B2
(45) Date of Patent: Aug. 18, 2026

(54) SYSTEMS AND METHODS OF COMMUNICATING THROUGH VISUAL OVERLAY FOR SURGICAL MEDICAL SYSTEMS

(71) Applicant: Auris Health, Inc., Redwood City, CA (US)

(72) Inventor: Samuel J. Malanowski, Menlo Park, CA (US)

(73) Assignee: Auris Health, Inc., Santa Clara, CA (US)

( * ) Notice: Subject to any disclaimer, the term of this patent is extended or adjusted under 35 U.S.C. 154(b) by 1065 days.

(21) Appl. No.: 17/331,546

(22) Filed: May 26, 2021

(65) Prior Publication Data

US 2021/0369370 A1 Dec. 2, 2021

Related U.S. Application Data

(60) Provisional application No. 63/031,356, filed on May 28, 2020.

(51) Int. Cl.
*A61B 34/00* (2016.01)
*A61B 17/29* (2006.01)
*A61B 90/00* (2016.01)

(52) U.S. Cl.
CPC .............. *A61B 34/70* (2016.02); *A61B 17/29* (2013.01); *A61B 90/39* (2016.02)

(58) Field of Classification Search
CPC ......... A61B 34/70; A61B 34/20; A61B 34/35; A61B 34/74
See application file for complete search history.

(56) References Cited

U.S. PATENT DOCUMENTS

| | | | | |
|---|---|---|---|---|
| 7,907,166 | B2 | 3/2011 | Lamprecht et al. | |
| 9,402,690 | B2 | 8/2016 | Zhao et al. | |
| 9,925,662 | B1 * | 3/2018 | Jules | G05B 19/423 |
| 2007/0156017 | A1 | 7/2007 | Lamprecht et al. | |
| 2007/0167702 | A1 | 7/2007 | Hasser et al. | |
| 2011/0050852 | A1 | 3/2011 | Lamprecht et al. | |
| 2011/0118752 | A1 * | 5/2011 | Itkowitz | B25J 9/1689 345/157 |
| 2013/0267838 | A1 * | 10/2013 | Fronk | A61B 5/064 600/424 |
| 2015/0025392 | A1 | 1/2015 | Zhao et al. | |
| 2019/0183591 | A1 * | 6/2019 | Johnson | B25J 9/1666 |
| 2021/0121245 | A1 * | 4/2021 | Hufford | A61B 90/361 |
| 2021/0145526 | A1 * | 5/2021 | Robinson | A61B 34/35 |
| 2021/0382559 | A1 * | 12/2021 | Segev | G06V 10/806 |
| 2022/0015851 | A1 * | 1/2022 | Itkowitz | G06F 3/011 |

FOREIGN PATENT DOCUMENTS

| | | | | |
|---|---|---|---|---|
| WO | WO-2020084625 A1 * | 4/2020 | | A61B 34/25 |

* cited by examiner

*Primary Examiner* — Sana Sahand
(74) *Attorney, Agent, or Firm* — FBT GIBBONS LLP

(57) ABSTRACT

A surgical system can include a master controller for controlling one or more surgical tools. The system can also include an input on the master controller configured to change the master controller from a first mode into a second mode. The first mode can be a teleoperation mode and the second mode can be a virtual marking mode. In the virtual marking mode, a user is capable of communicating a virtual marker to other staff.

19 Claims, 29 Drawing Sheets

SYSTEMS AND METHODS OF COMMUNICATING THROUGH VISUAL OVERLAY FOR SURGICAL MEDICAL SYSTEMS

CROSS-REFERENCE TO RELATED APPLICATIONS

This application claims the benefit of U.S. Provisional Application No. 63/031,356, tiled May 28, 2020, entitled "Systems and Methods of Communicating Through Visual Overlay for Surgical Medical Systems," which is hereby incorporated by reference in its entirety.

TECHNICAL FIELD

This application is directed to robotic medical systems, and more particularly to visual overlays configured for use with robotic medical systems.

BACKGROUND

Medical procedures, such as laparoscopy or endoscopy, may involve accessing and visualizing an internal region of a patient. In a laparoscopic procedure, for example, a medical instrument can be inserted into an internal region through a laparoscopic access port. Robotically-enabled medical system can be used to perform such medical procedures. The robotically-enabled medical systems may include several robotic components, including, for example, robotic arms, robotic instrument manipulators, and robotic medical instruments, such as robotically controllable laparoscopes or endoscopes. The robotically-enabled medical systems can be controlled using a user console that may include one or more hand operated inputs as well as one or more foot operated inputs.

SUMMARY

The systems, methods and devices of this disclosure each have several innovative aspects, no single one of which is solely responsible for the desirable attributes disclosed herein.

In a first aspect, a surgical system includes a master controller for controlling one or more surgical tools and an input on the master controller configured to change the master controller from a first mode into a second mode. The first mode can include a teleoperation mode and the second mode can include a virtual marking mode. The input can include a button on the master controller. The input can include an action of one or more of the graspers of the master controller. The action can include a double gripping of at least one of the graspers of the master controller. In the virtual marking mode, a user can be capable of communicating a virtual marker to other staff The virtual marker can include a hand-drawn overlay positioned over a representation of a surgical site. The virtual marker can be capable of display on one or more of a viewer on the master controller, a screen of a tower, or a screen.

In another aspect, a surgical system for communication can include a master controller for controlling one or more surgical tools and an input on the master controller for receiving an input from the user configured to produce a virtual marker. The virtual marker can be configured to be communicated and displayed on a first display. The virtual marker can be configured to be communicated and displayed on a second display. The virtual marker can be configured to highlight an area of interest in a surgical site. The virtual marker can be configured to be saved or recorded for later review. The virtual marker can be registered to an anatomical space. The virtual marker can be fixed or held in an anatomical space, such that the virtual marker remains fixed in place to the anatomical space when a camera view is changed.

Another aspect relates to a method of communication during surgery, the method including: displaying a representation of a surgical site at a master controller, the master controller including a viewer for displaying the representation and an input to control one or more surgical tools; receiving a user command to generate and position a virtual marker; and overlaying the virtual marker on the representation of the surgical site. The method may further include registering the virtual marker to a fixed point in the representation of the surgical site. The method may further include fixing the virtual marker to a point in the representation of the surgical site, wherein the virtual marker remains fixed to the point in the representation of the surgical site when the camera view changes. The method may further include displaying the virtual marker on the representation of the surgical site on at least one or more of a display of a master controller, a viewing screen of a tower, or a screen. The method may further include communicating the visual marker on the representation of the surgical site to at least two users in two different locations. The user command can be based on a user actuation of one or more graspers of a master controller. The user actuation can include movement of a user's finger on a screen. The user actuation can include movement of the one or more graspers of the master controller. The method can further include activating a virtual marking mode based on a user actuation. The user actuation can include actuation of a button on a master controller. The user actuation can include selecting the virtual marking mode in a menu. The user actuation can include pressing a foot pedal. The user actuation can include an action of one or more of graspers of a master controller. The action can include a double gripping of one or more graspers of a master controller.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations, Headings are included herein for reference and to aid in locating various sections. These headings are not intended to limit the scope of the concepts described with respect thereto. Such concepts may have applicability throughout the entire specification.

A. Robotic System—Cart.

Figure 1:
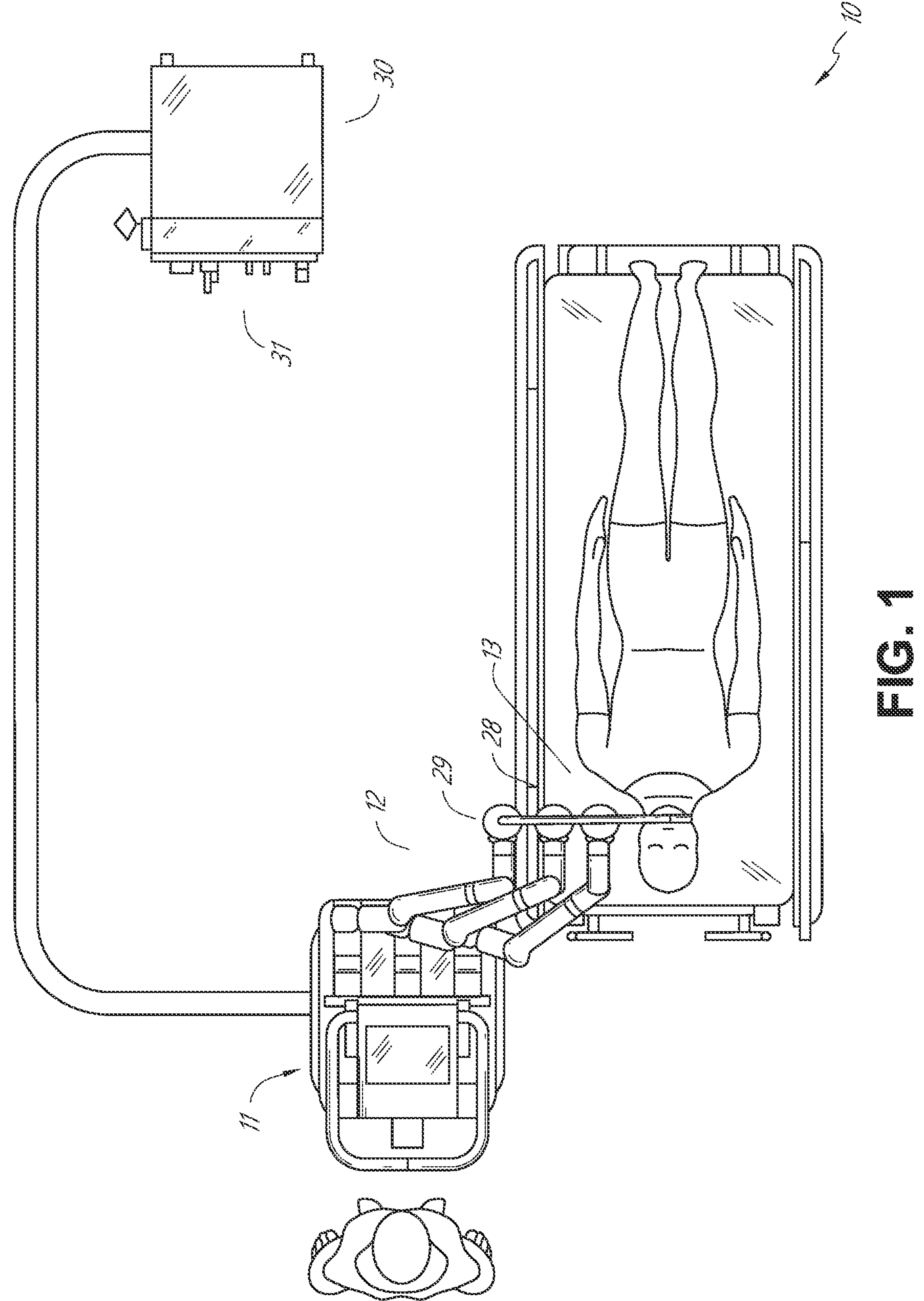
FIG. 1 illustrates an embodiment of a cart-based robotic system arranged for diagnostic and/or therapeutic bronchoscopy.
Figure 2:
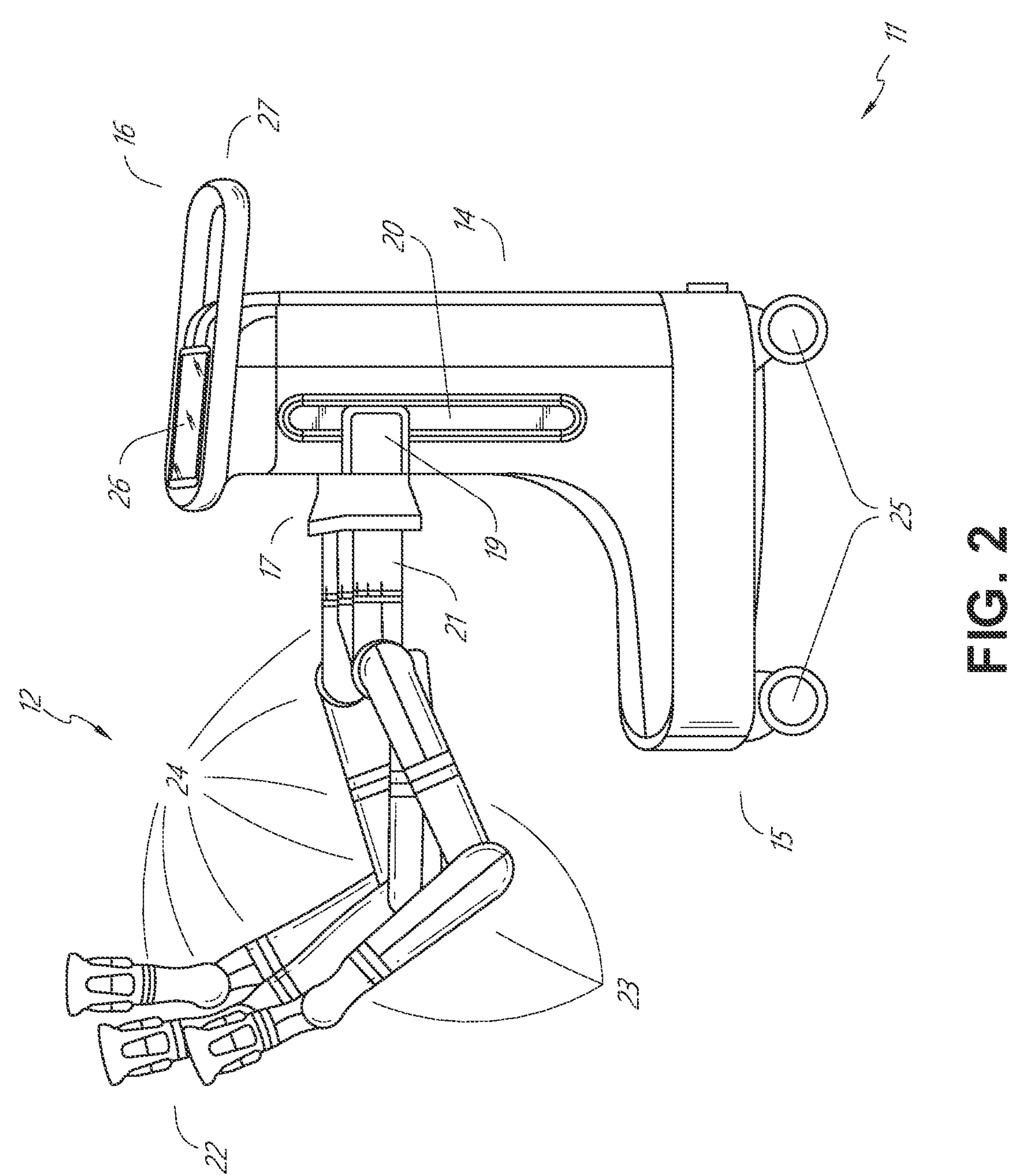
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15, Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
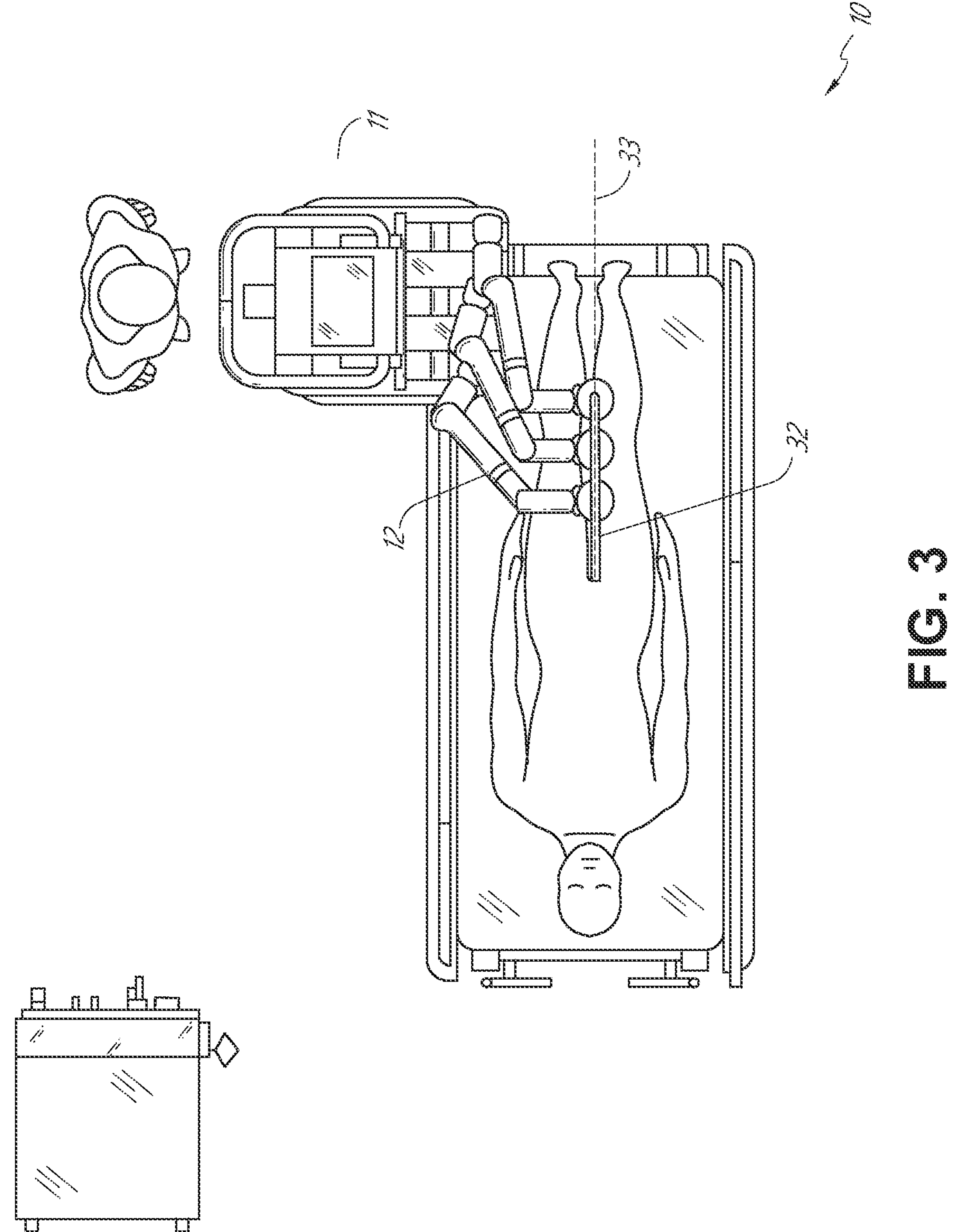
FIG. 3 illustrates an embodiment of the robotic system of FIG. 1 arranged for ureteroscopy.

FIG. 3 illustrates an embodiment of a rohotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, meters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
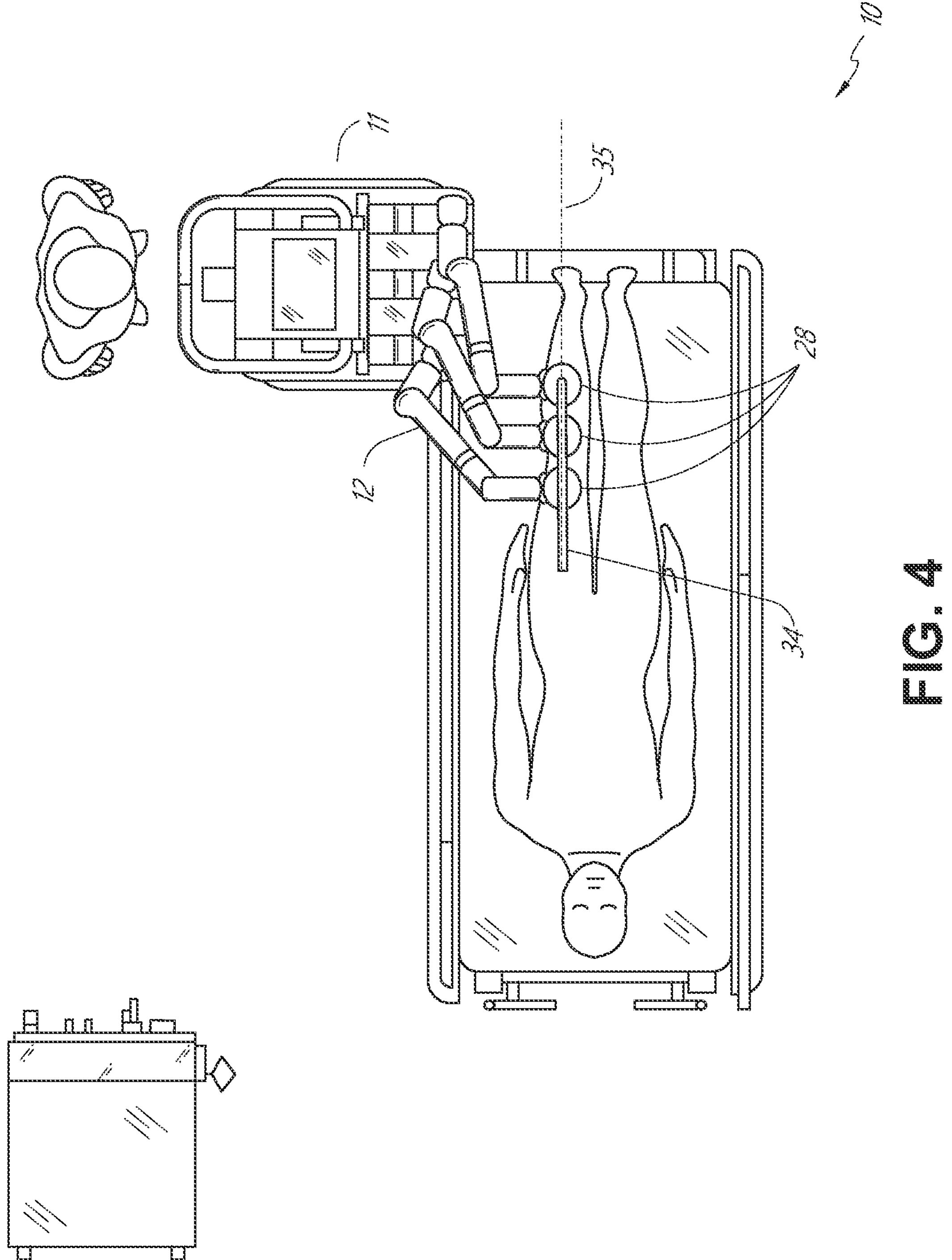
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
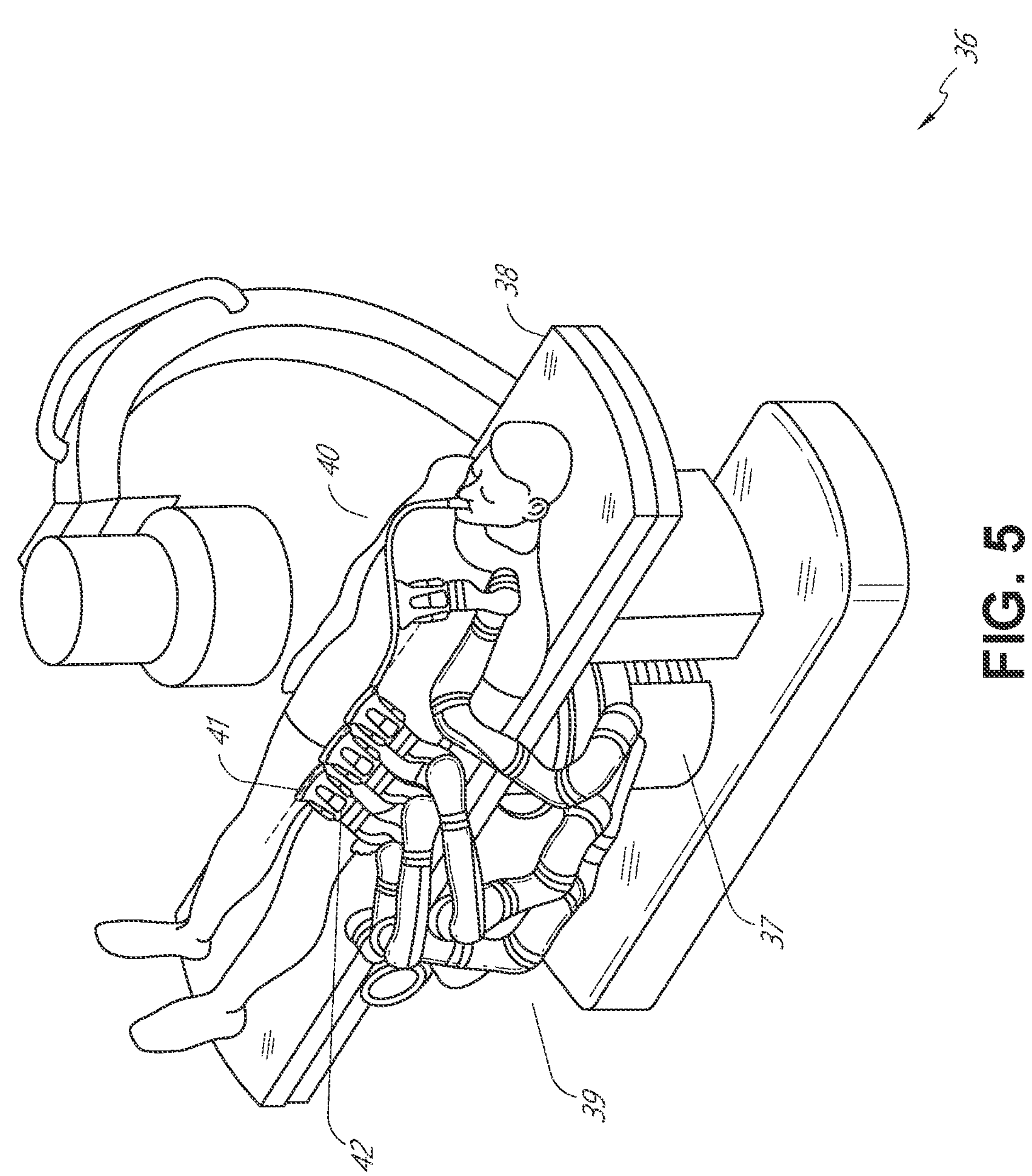
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
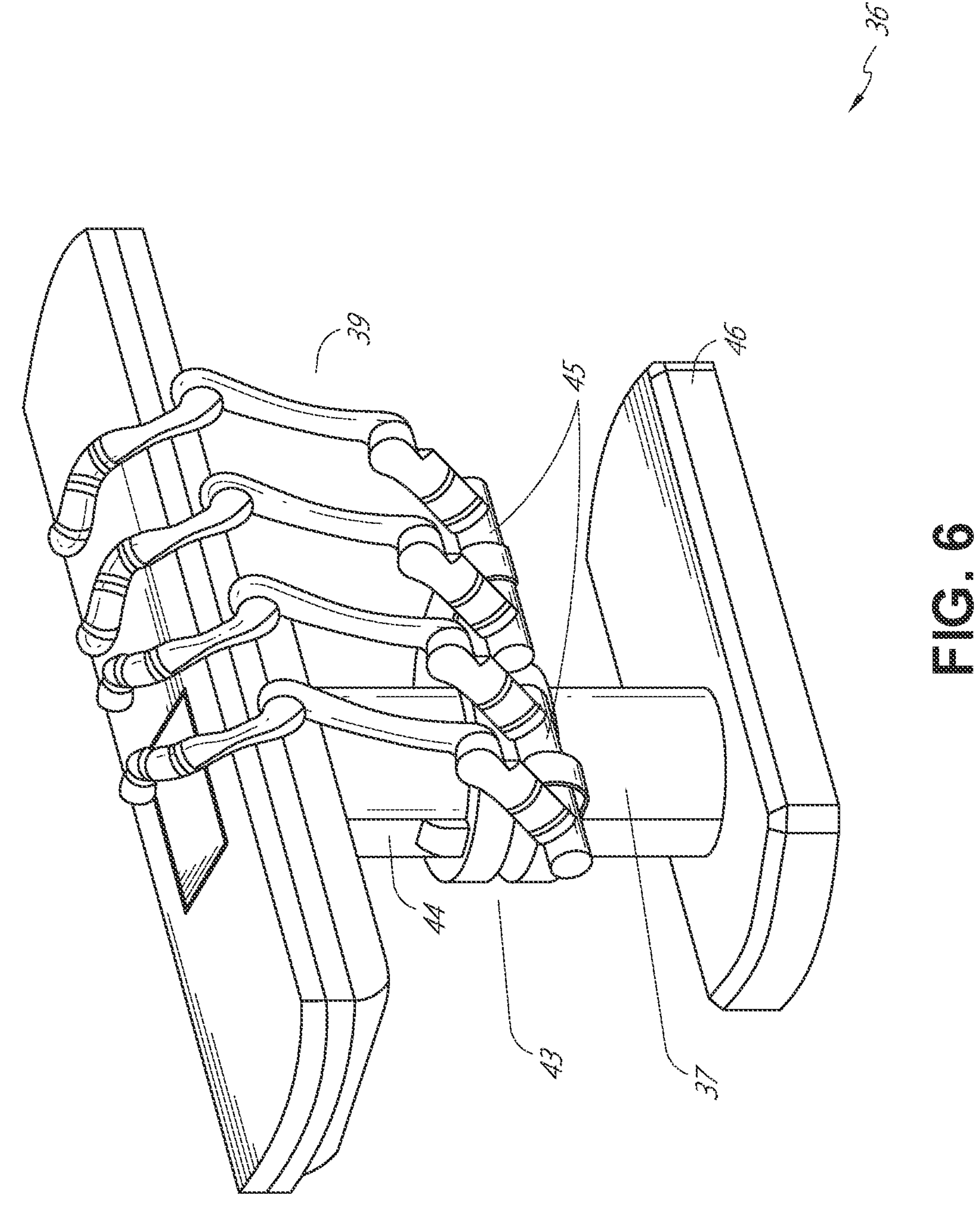
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
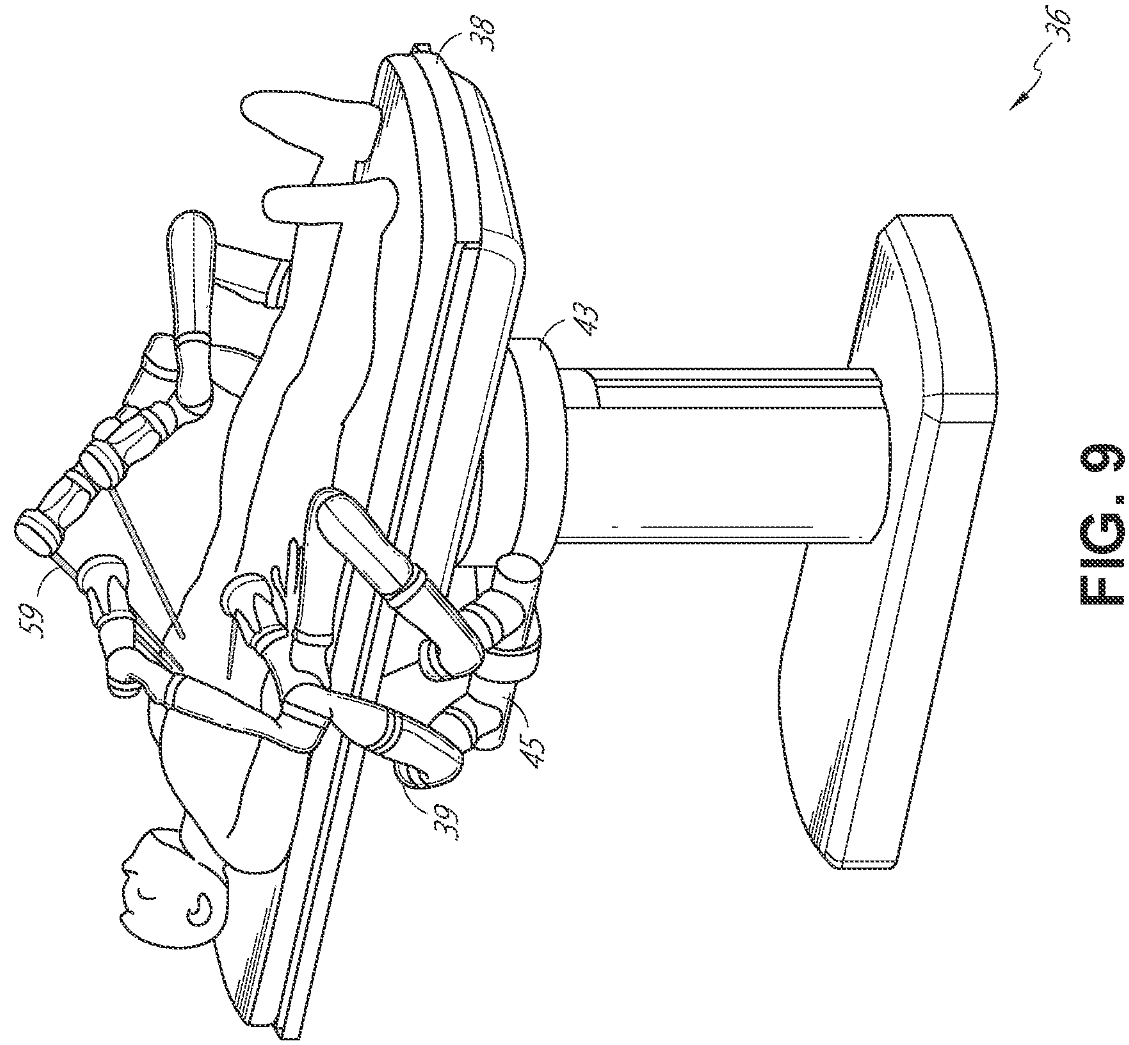
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures, Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
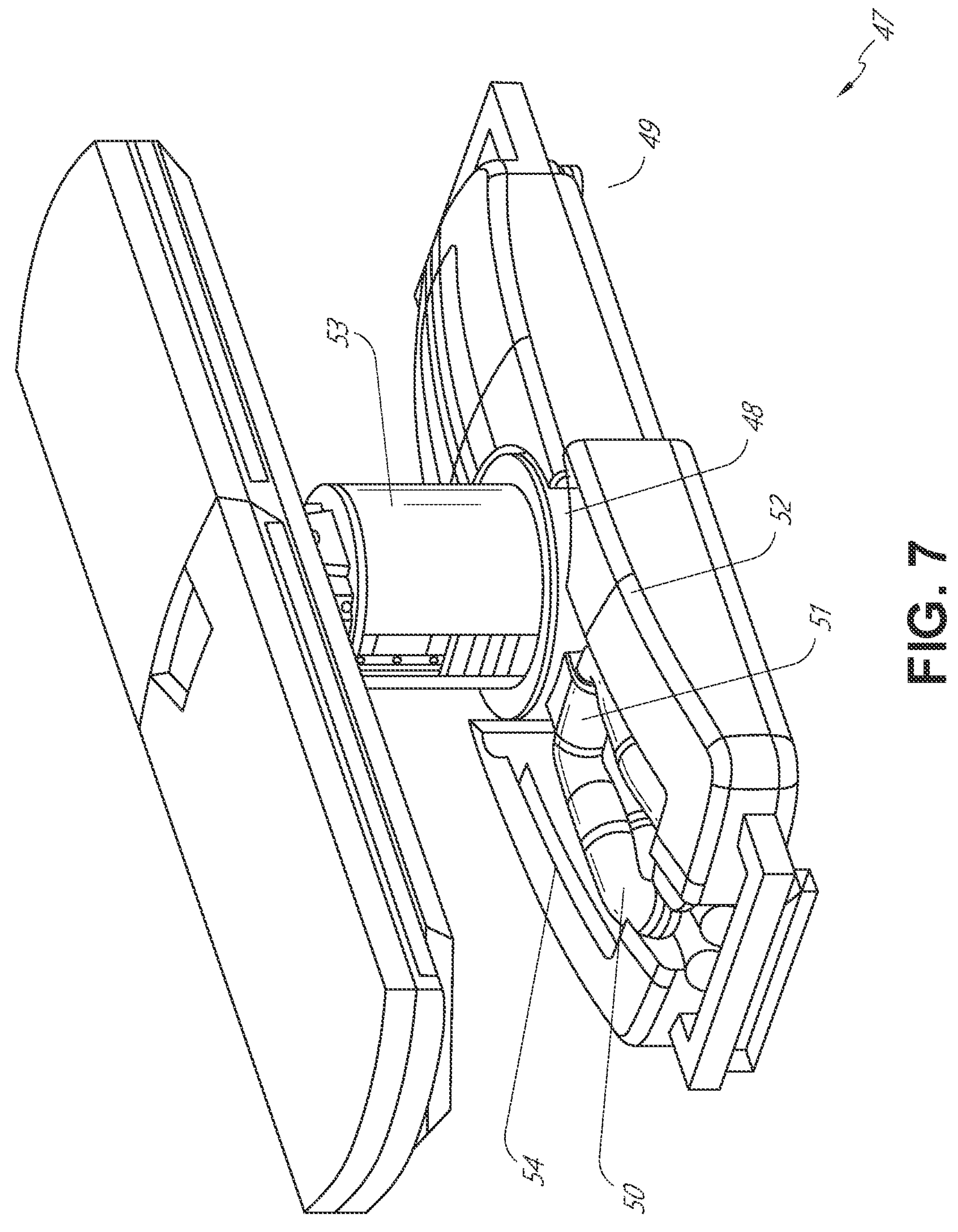
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49, Base covers 52 may be translated and retracted open to deploy the carriages 48, arm mounts 51, and robotic arms 50 around column 53, and closed to stow to protect them When not in use. The base covers 52 may be sealed with a membrane 54 along the edges of its opening to prevent dirt and fluid ingress when closed.

Figure 8:
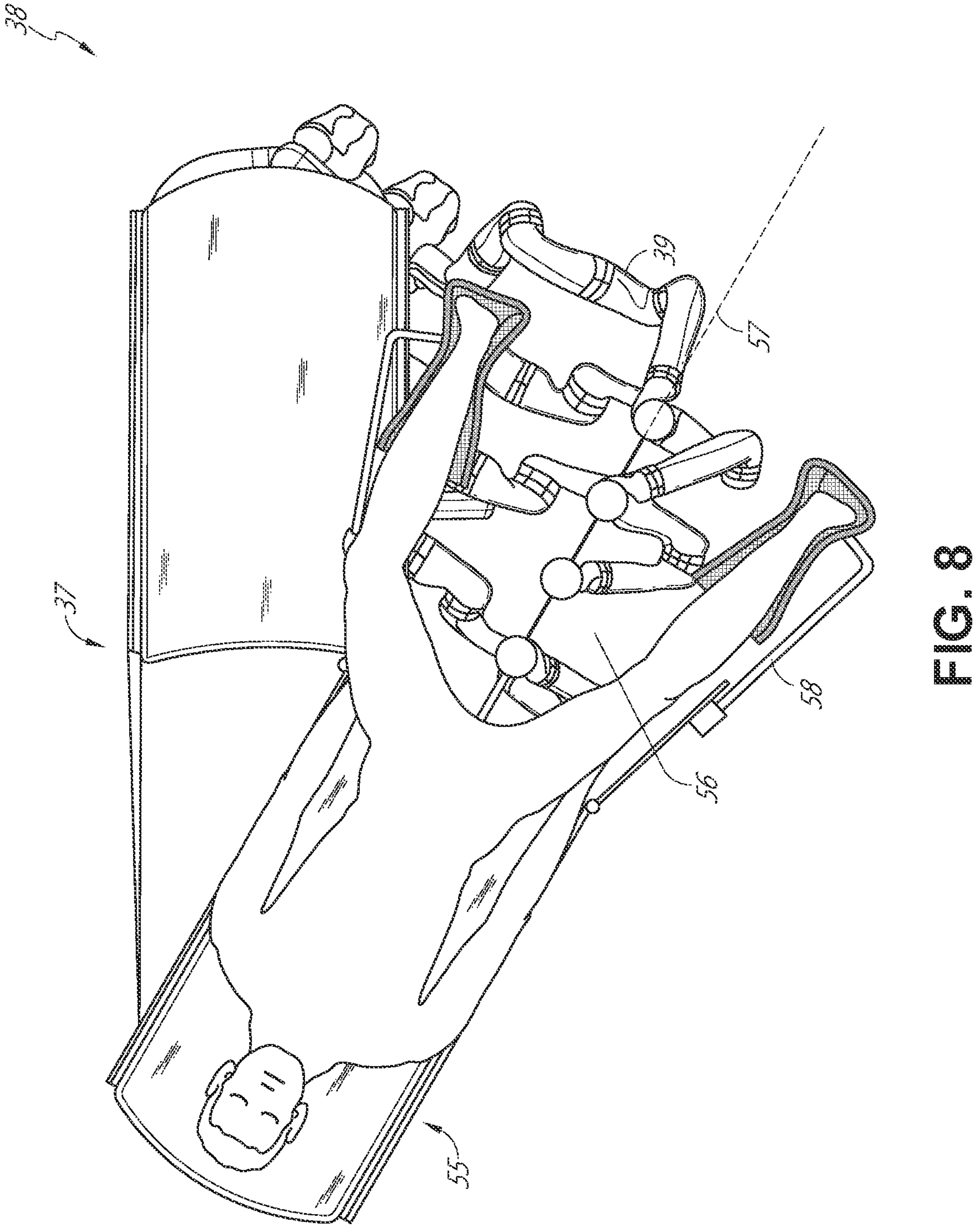
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
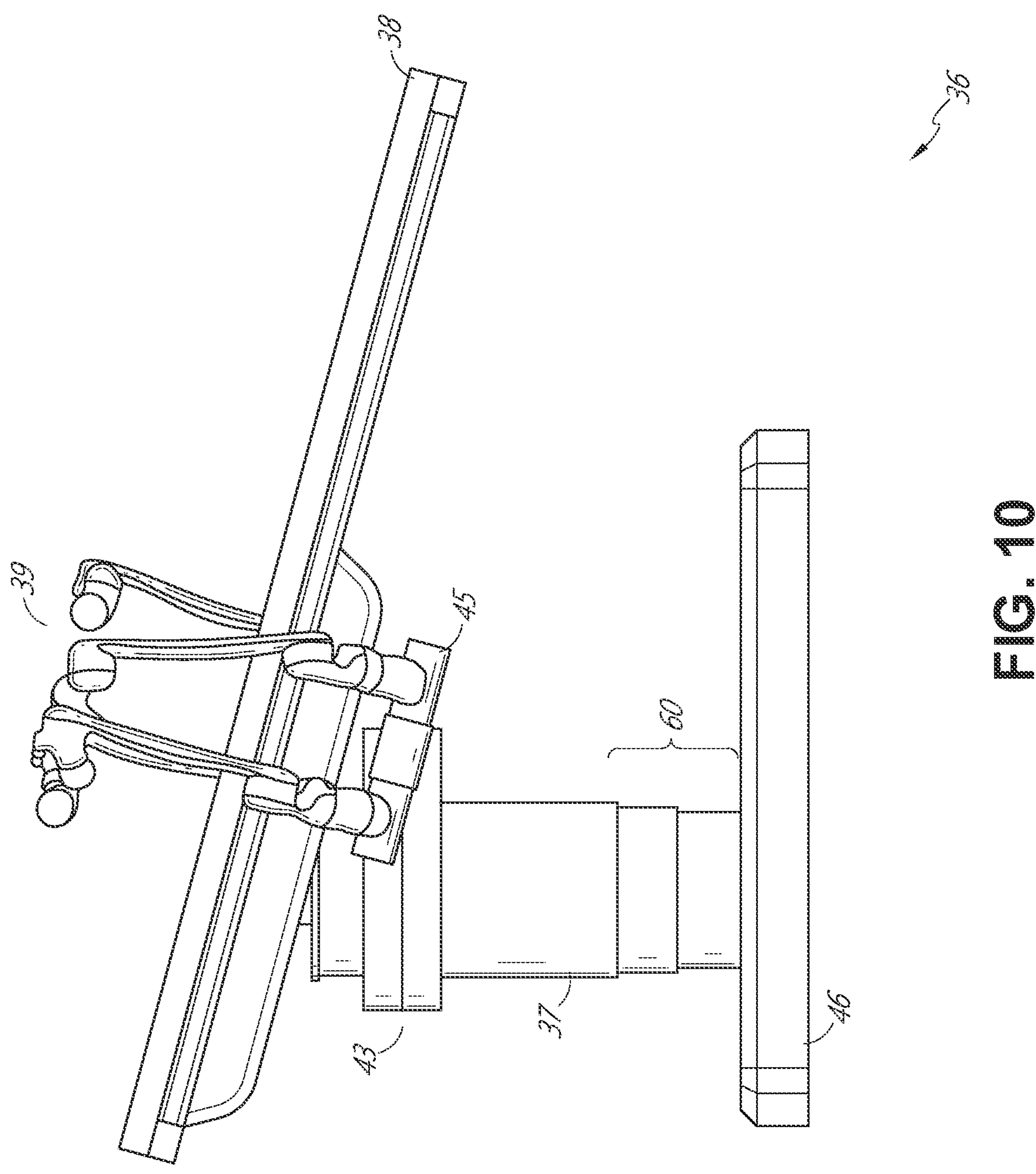
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
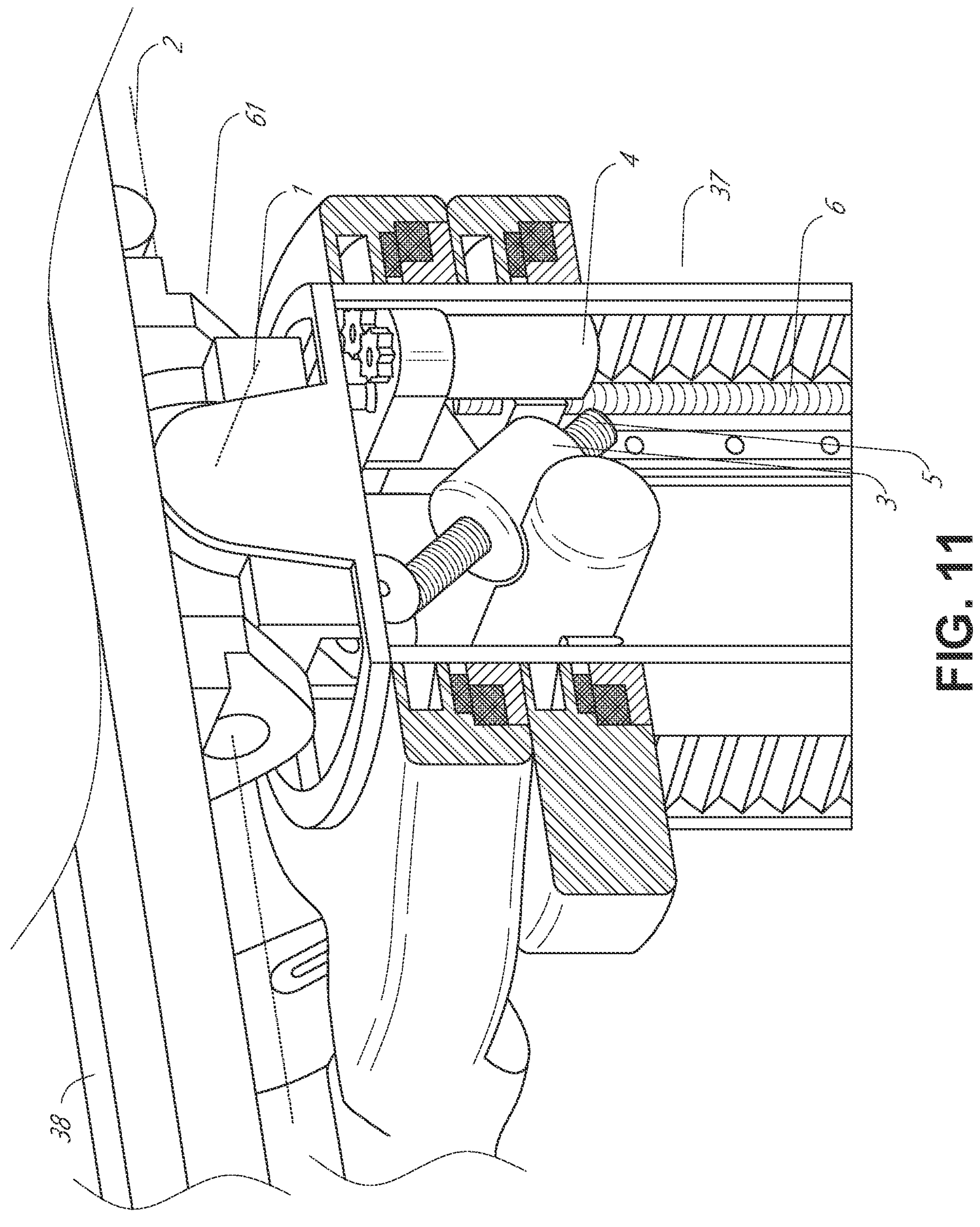
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
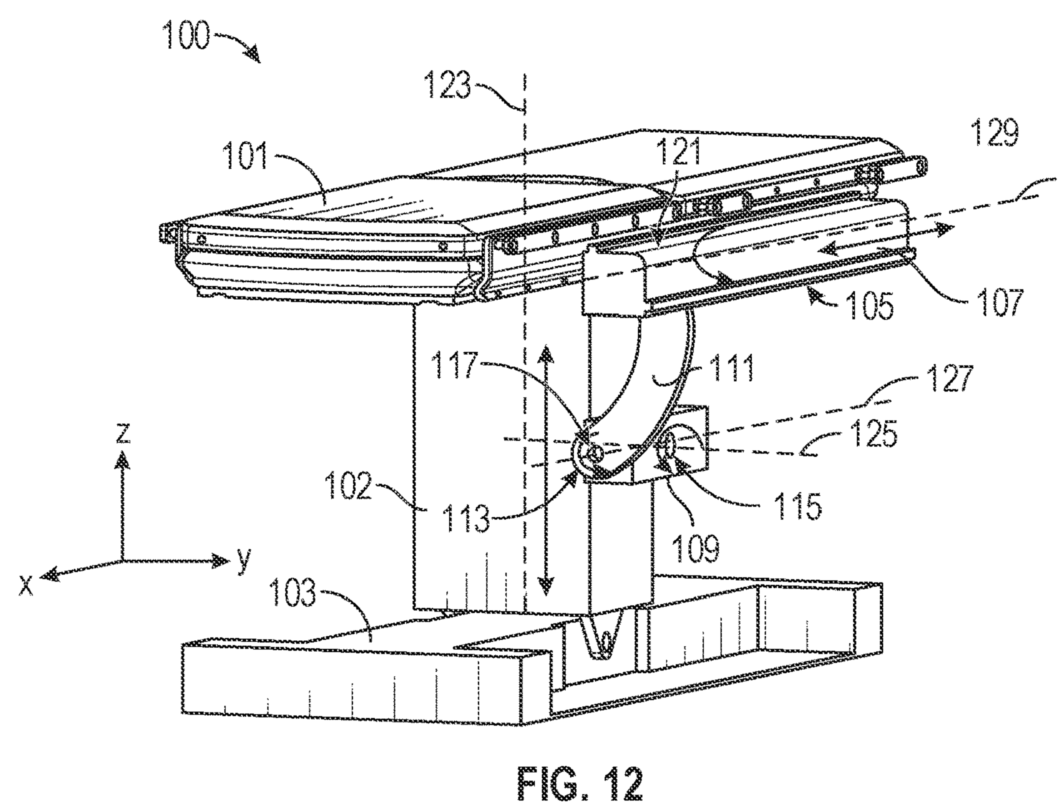
FIG. 12 illustrates an alternative embodiment of a table-based robotic system.
Figure 13:
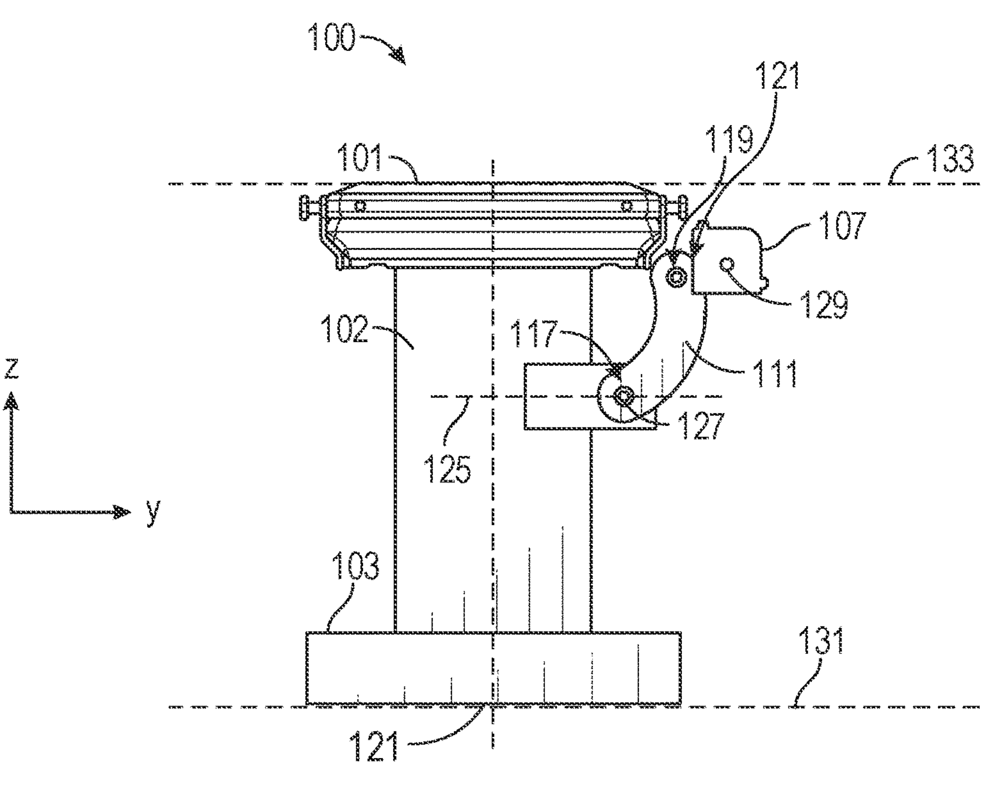
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can all the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
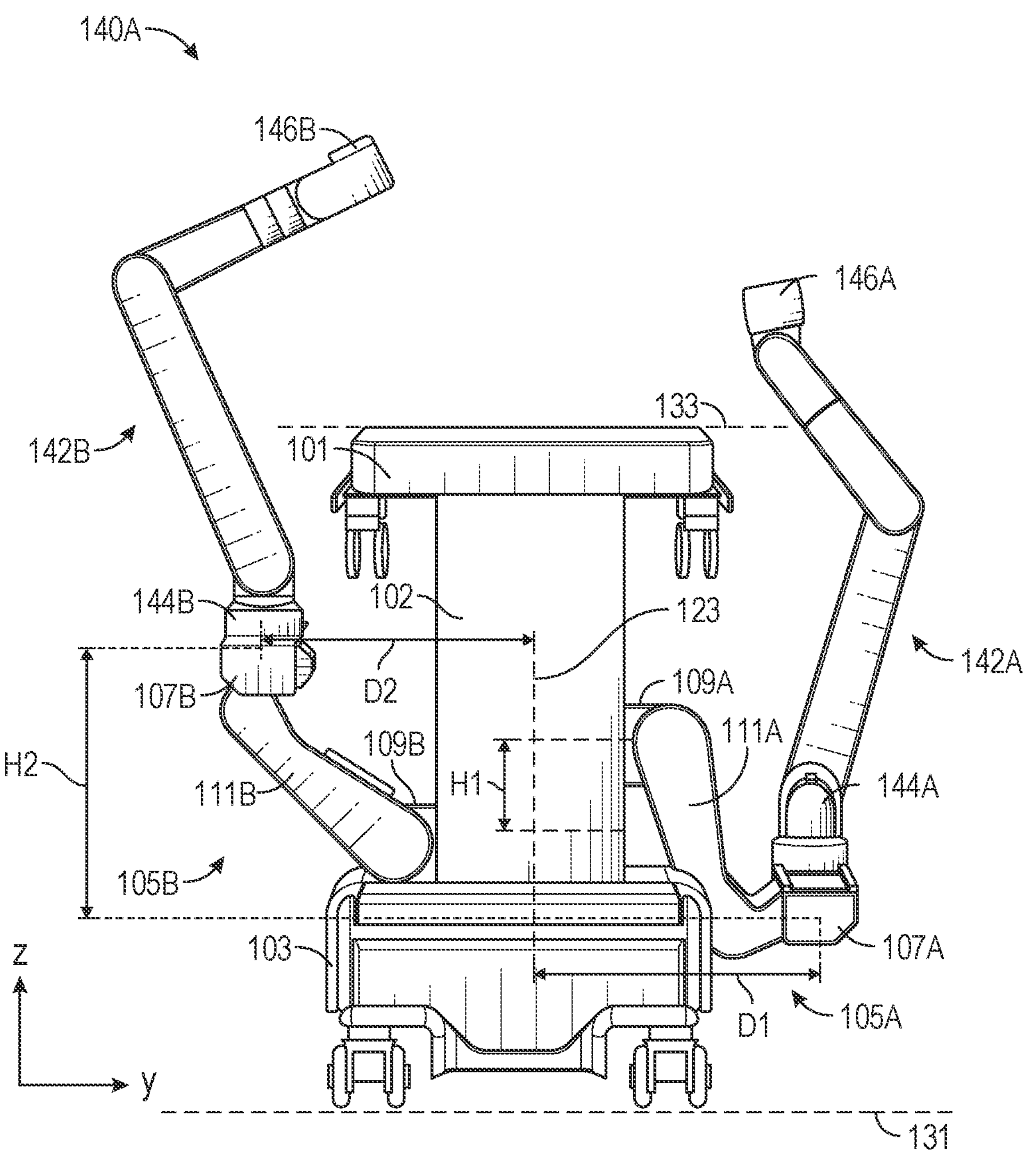
FIG. 14 illustrates an end view of a table-based robotic system with robotic aims attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In sonic embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
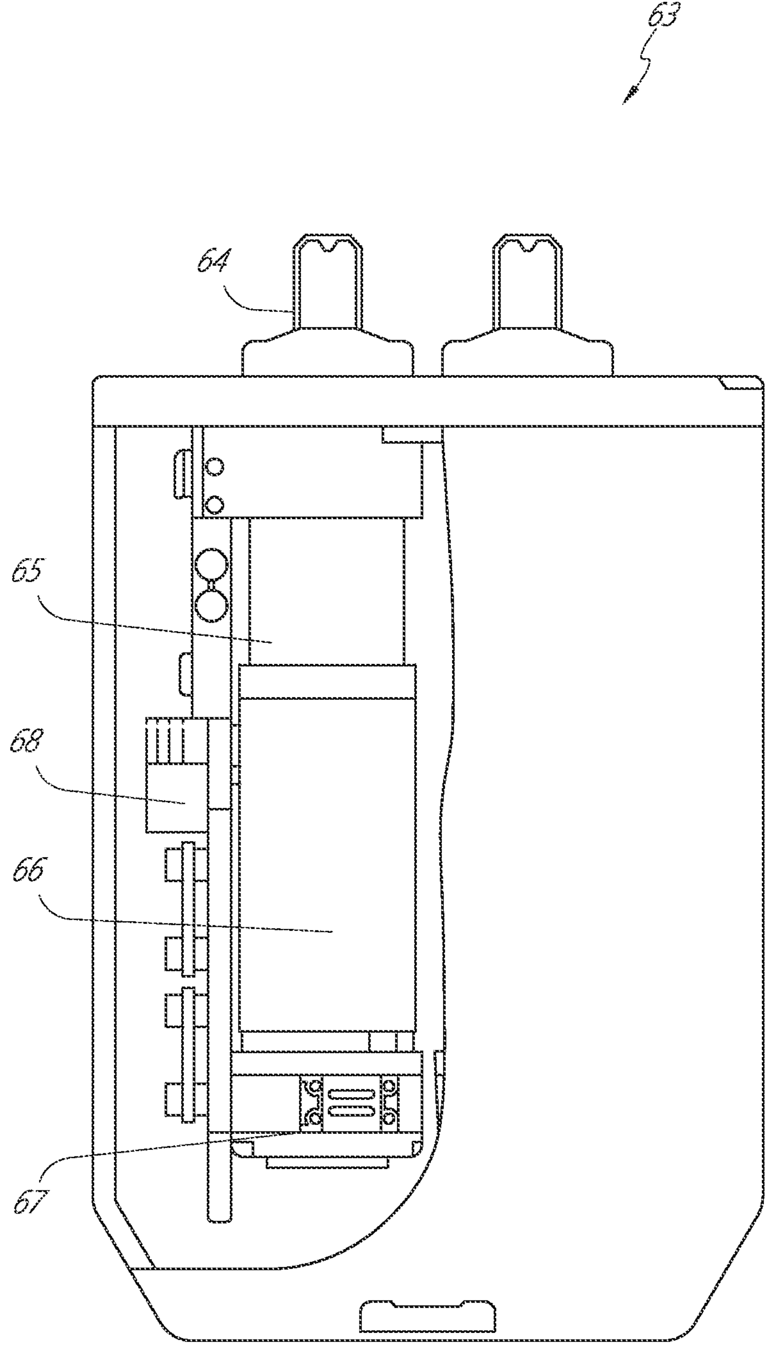
FIG. 15 illustrates an exemplary instrument driver.
Figure 15:

FIG. 15 illustrates an example instrument driver, Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
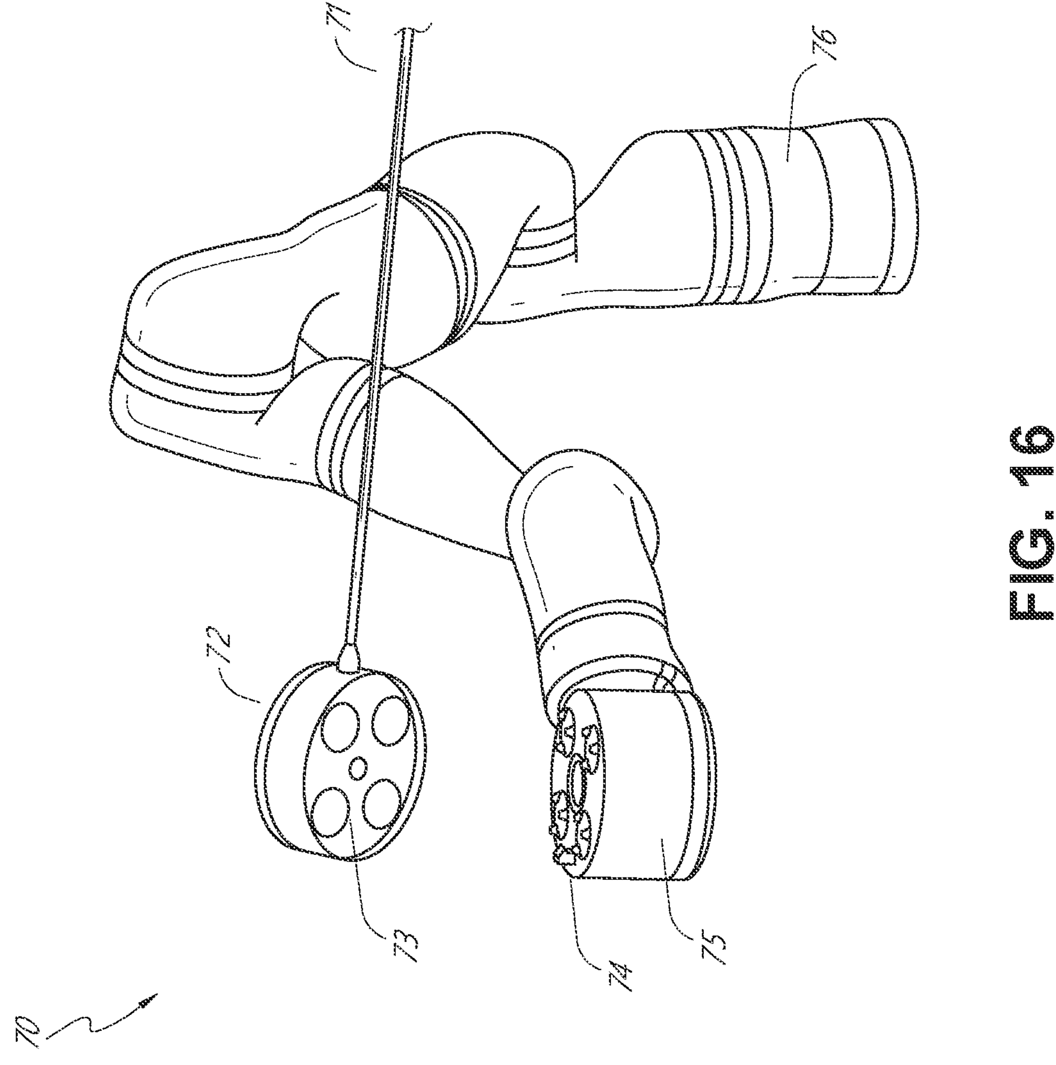
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shall compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shall 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
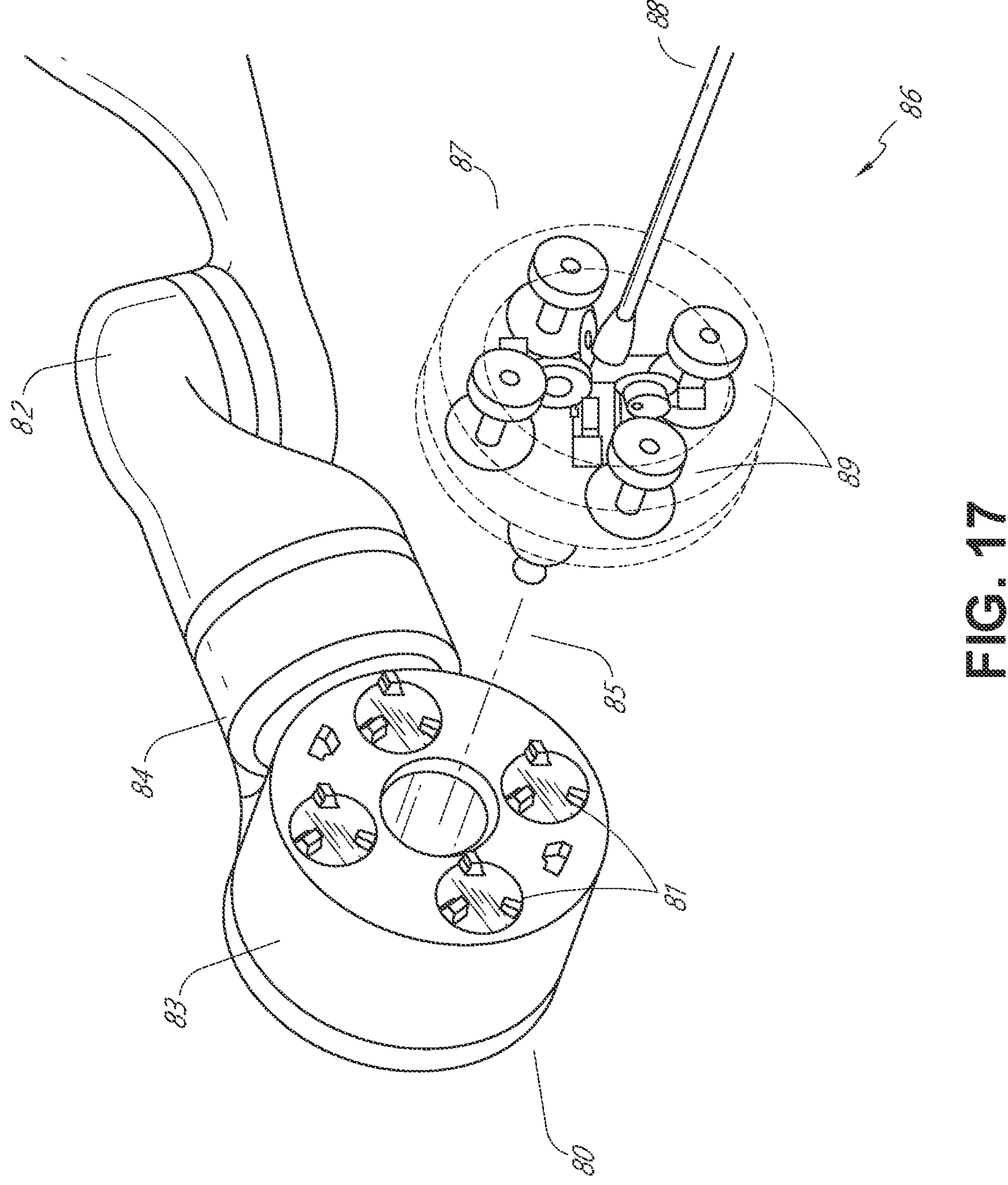
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
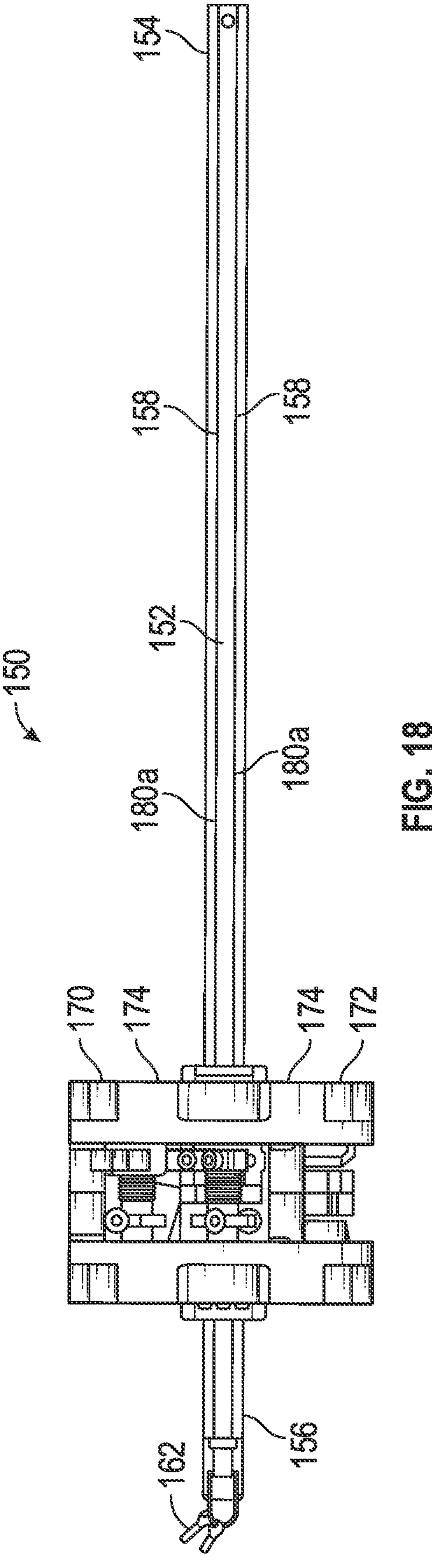
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152.

Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
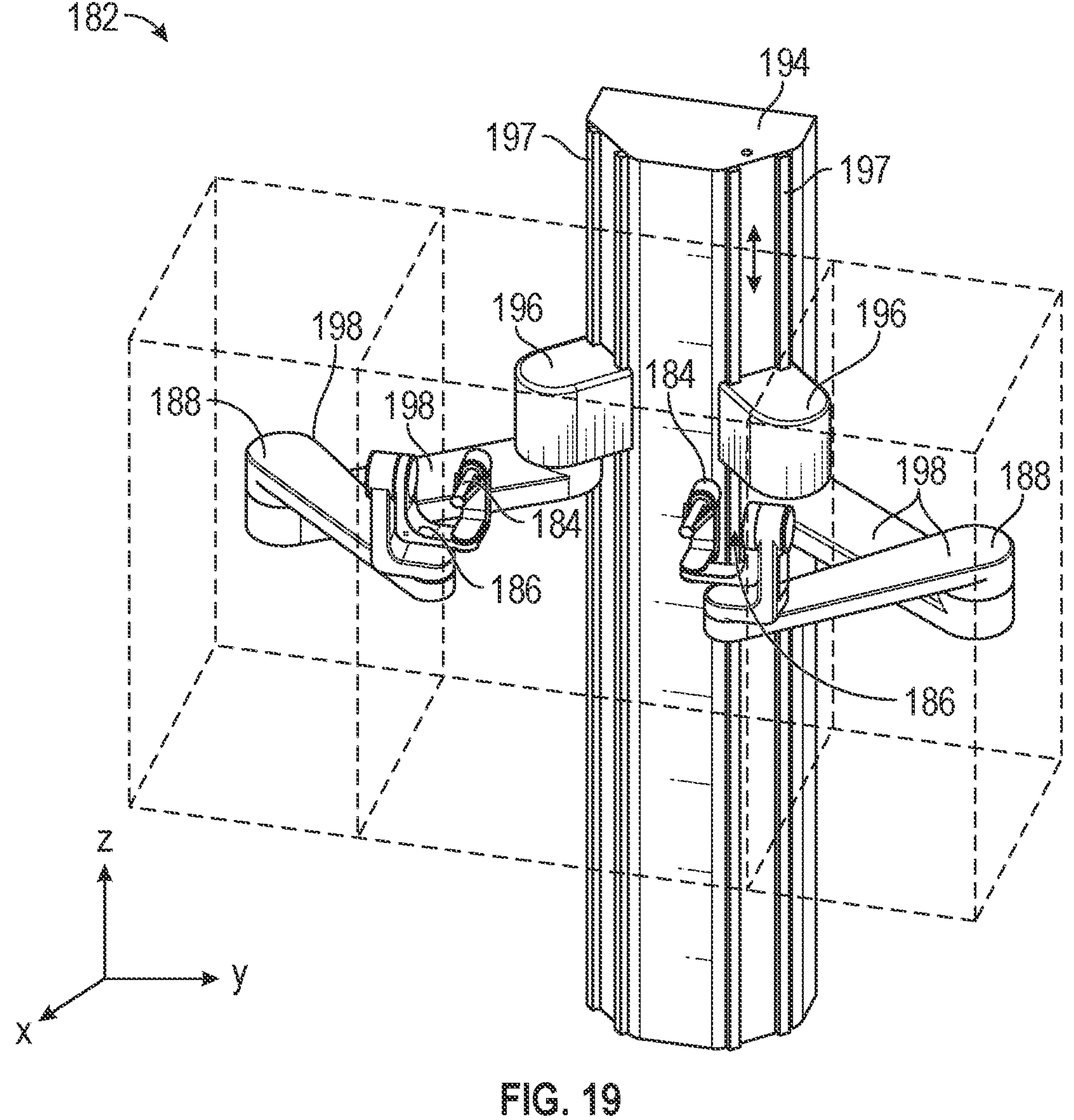
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
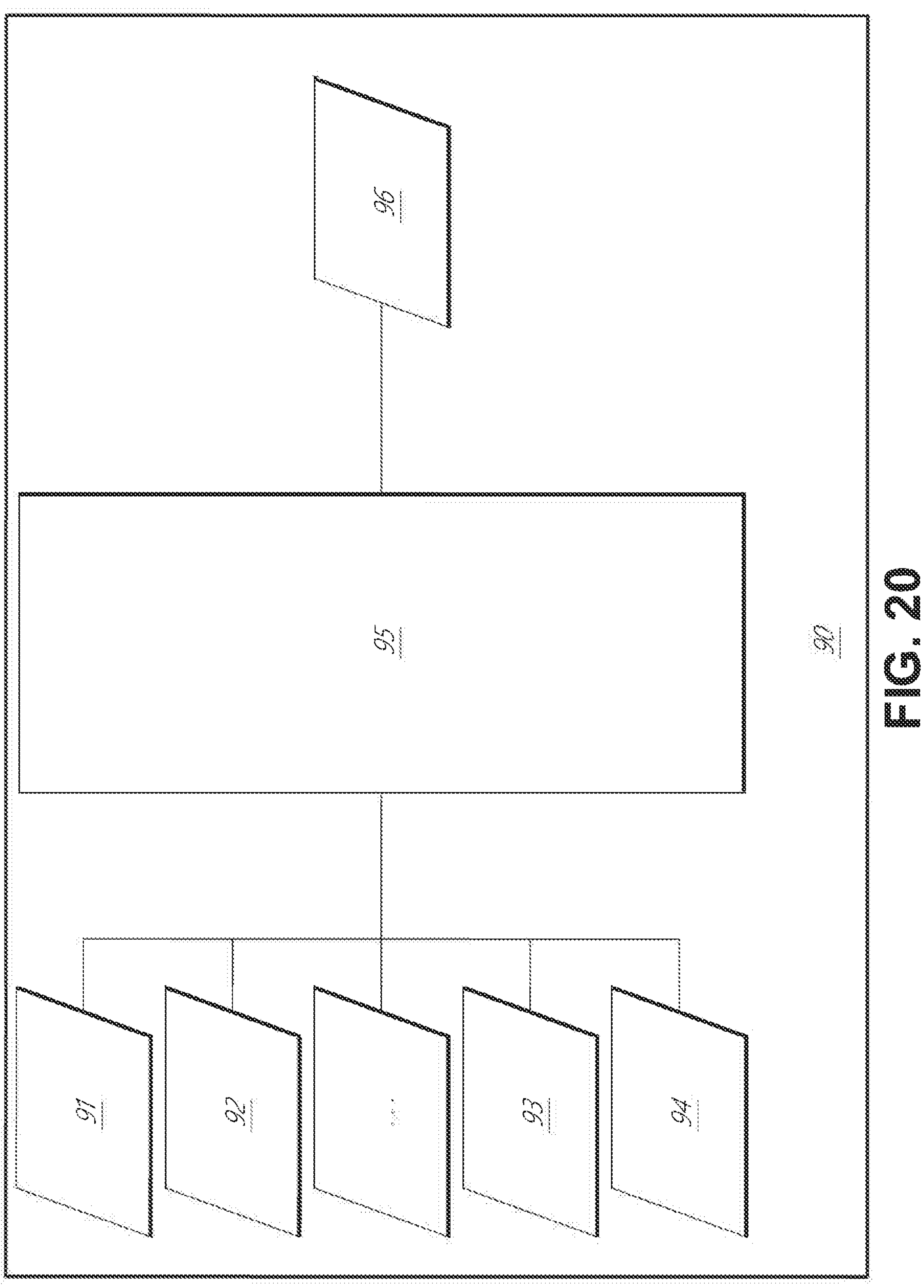
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera. (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static FM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Visual Overlays for Communication

Robotic medical systems, such as those described above with reference to FIGS. 1-20 and others, can include virtual markers as visual overlays displayed on a display of one or more viewers or screens. For example, a robotic medical system can include one or more screens which can include a display to be configured to communicate or provide information about the system to a user or medical personnel or staff in an operating room. The visual overlays may also be known as image overlays or virtual overlays. The visual markers can include telestrations, image markers, virtual markers, visual indicators, image indicators, or virtual indicators. For example, the one or more viewers of the robotic medical system can include the console 31 of tower 30 as shown in FIG. 1 or the touchscreen 26 of cart 11 as shown in FIG. 2.

Such virtual markers can be particularly useful for robotic medical systems that include several components and associated staff. For example, a surgeon can be positioned at a surgeon console, which can sequester or isolate the surgeon from other staff in the room. Some surgeons can attempt to communicate to the rest of the staff through audio commands, such as shouting across a room. Some surgeons can attempt to communicate to the rest of the staff through visual commands, such as by pointing with a tip of an instrument, which can be seen on a monitor visible by staff. However, these methods are not always reliable or possible. Additionally, these methods may not always be effective or provide for dual or two-way communication between users, such as between surgeon and staff For example, the staff may view the instrument in a patient side monitor. However, it can be difficult for the staff to understand instructions or identify the physical structures which are being pointed out, particularly if 3-D vision is not available. Furthermore, there may be no way for the staff to communicate back to the surgeon.

It can therefore be advantageous and clinically significant to provide a method for two-way or dual communication between the users through virtual markers. For example, if a surgeon is removing a lesion or cancerous area in the anatomy, the surgeon may want to highlight the area for removal. The surgeon, isolated in the surgeon console, can generate a visual marker which can be configured as a visual overlay on an image, which may be an image of the treatment site. The virtual marker ma then be displayed on the screen of the surgeon's console and on one or more screens for other staff to view. For example, the virtual markers of an image can be displayed on a display of a viewer, screen of a tower and/or a patient platform. In some examples, the display which can include the virtual marker can be shown remotely, such as to individuals not inside the room. In some examples, the virtual markers can be saved for review for later review. The virtual markers can be displayed to at least two users in two different locations. The virtual marker can also be displayed to more than two users in more than two different locations.

This can advantageously allow reliable and understandable communication between the surgeon and the staff or between staff. Such communication between the surgeon to the staff is novel. The method of communication can be integrated in components already used in the system for other purposes and thus can be comfortably used by the users. The use of virtual markers can also be convenient and be conducted without interrupting the procedure flow or without requiring the surgeon to leave the surgeon console.

The virtual markers can advantageously be used in a number of ways and positioned in various components of the robotic system. The virtual markers can be displayed in one or more screens of the medical system, such as, for example, a user/surgeon console, a tower console 31, a cart touchscreen 26, or a screen in a patient bedside monitor.

The virtual markers can also be used to highlight or mark an area of interest, such as a lesion or cancerous area. The surgeon may wish to communicate the area of interest to staff and provide a highlight or identification of the area of interest. For example, the surgeon can use virtual marking or telestration to point out potential hazards, such as blood vessels to avoid. Virtual markers can also be used to identify desired placement of manual assistance, such as stapling or suturing or other equipment. In some examples, virtual markers can also be used to serve as documentation of a surgery for later review.

Another use of the telestration or virtual marking may be for training. This may allow the surgeon to communicate and train another user. For example, if the other user does not have a stereoscopic view, telestration or virtual marking would allow a surgeon to communicate to the other user.

The illustrated examples of the virtual markers are provided by way of example, not limitation. The illustrated examples are shown as hand drawn markings, such as circles or lines, by way of example, not limitation. For example, the virtual markers may also be various shapes, symbols, words, text, or predefined shapes. Further, not all virtual markers need be included in all embodiments. For example, in some embodiments, one or more of the virtual markers may be omitted from the viewer. The illustrated embodiments are provided by way of example and illustration and are not intended to be limiting. Upon consideration of this disclosure, one of skill in the art will appreciate that other configurations and embodiments, which are within the scope of this disclosure for systems with virtual markers are possible. Further, several notable advantages of virtual markers for use with robotic medical systems will be described below. Not all of the described advantages need be provided by every embodiment, and the virtual markers may also provide advantages that are not described herein.

The virtual markers can be positioned in various places. In some examples, the virtual markers can be displayed on viewers, which may be a display or screen for displaying text, images or other symbols. The viewers as described can be positioned on a number of locations, such as a head-in viewers (2D or 3D), viewers of the master controller, operating room monitors, console monitors, touchscreens, tower consoles, user input displays, patient side interfaces, or a screen. In some embodiments, the virtual markers can be configured to include different patterns, colors, brightness, or intensity. In some embodiments, the virtual indicators can be configured to change patterns (e.g., a blinking or flashing pattern) and/or change intensity or brightness.

Figure 21:
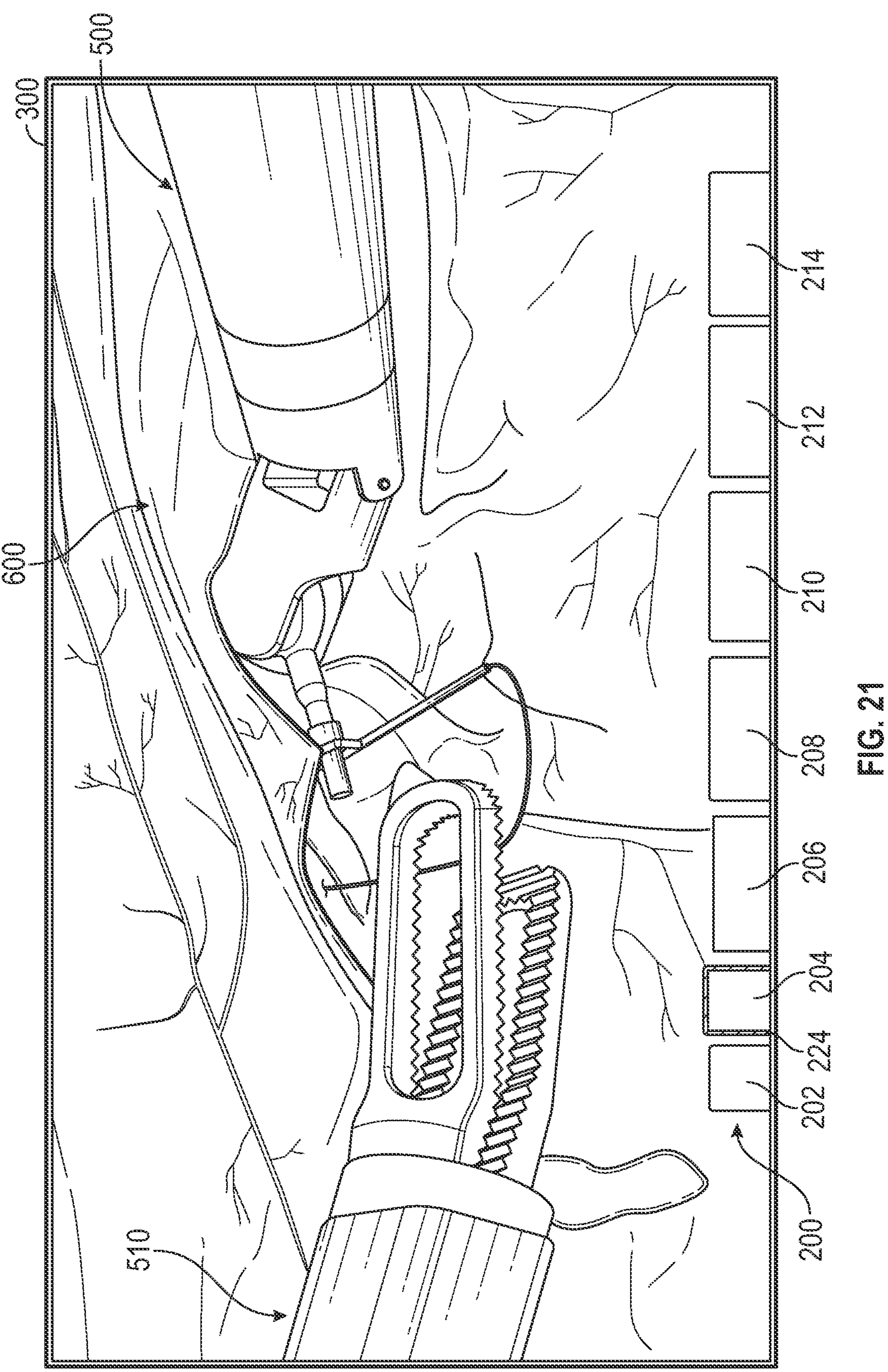
FIG. 21 illustrates an example of a viewer with a menu including a telestration mode.

FIG. 21 illustrates exemplary embodiments of a display of a viewer 300 that may be used to display one or more virtual markers. The display of the viewer 300 can include a rendering of an image or representation (graphical or otherwise) of one or more medical instruments 500, 510. The display of the viewer 300 can include a rendering of an image or representation (graphical or otherwise) of one or more medical instruments 500, 510. The display of the viewer 300 can also include an image or representation (graphical or otherwise) of the patient anatomy including the treatment site 600. The display of the viewer 300 can be configured to display or render an image or representation of at least a portion of one or more medical instrument 500, 510 at a treatment site 600.

The viewer 300 can be configured to allow the user (e.g., a surgeon) to view images of a treatment site 600 from one or more imaging devices (e.g., cameras) of the robotic system in order to facilitate control of the system to perform a robotic medical procedure. For example, a robotically-controllable endoscope of the robotic system can include a camera positioned at a distal tip thereof. The user can view an image from the camera of the endoscope in the viewer 300 in order to facilitate control of the endoscope and/or other components of the robotic medical system. As another example, the robotic system may include one or more cameras laparoscopically or endoscopically inserted into a patient. The user can view images from the inserted cameras in order to facilitate control of one or more additional robotically-controlled medical instruments, such as one or more additional laparoscopically inserted medical instruments, such as the medical instruments 500, 510 as shown. The viewer 300 can include a screen for viewing the images from the one or more cameras.

FIG. 21 also shows a menu or series of tabs 200, which may be image or visual overlays positioned on an image or representation of a treatment site 600 within a patient of the viewer 300. Each of the series of tabs 200 can be associated with different modes for operation, different instruments, and/or different functions. The series of tabs 200 can include any number of tabs. For example, a series of tabs 200 are shown in FIG. 21, including a first tab 202, a second tab 204, a third tab 206, a fourth tab 208, a fifth tab 210, a sixth tab 212, and a seventh tab 214. The first tab 202 can be associated with a teleoperation mode. The second tab 204 can be associated with a telestration mode. The surgeon can operate in a first mode, such as a teleoperation mode Where the surgeon can move or actuate the one or more medical instruments 500, 510 within the treatment site 600. The surgeon can then use the series of tabs 200 by selecting the second tab 204 to switch from the first mode to a second mode, which may be a virtual marking mode or telestration mode.

The associated tab of a certain mode can be bolded, highlighted, enlarged, or otherwise differentiated when a user input (e.g. controller 182) is in or selects the associated mode of operation. For example, the second tab 204, when selected, can be shown as the active mode with an indicator 224 positioned around the second tab 204. In some examples, each of the series of tabs 200 may be selectable or clickable, where selecting or clicking a particular tab, the associated mode of operation can be activated. The menu or series of tabs 200 can be positioned anywhere on the viewer 300. As shown in the illustrated example in FIG. 21, menu or series of tabs 200 can be positioned on the bottom side of the viewer 300.

As noted above, the system can include one or more controllers configured to be operated by the user in order to provide control of various aspects or components of the robotic medical system. The one or more controllers can include gimbals or pedals. Examples of such controllers 182 have been described above with reference to FIG. 19. In related aspects, one or more of the controllers can be configured to selectively couple and control medical instruments. For example, the one or more controllers can be configured to allow a user to fire or activate a thermal/heat feature (e.g., cauterizing, sealing, etc.), staple, clip, suture, cut, grasp, or any function of a medical instrument. The controllers can be configured to perform or activate different functions of the instruments (e.g., cut, grasp, coagulate, seal, clip, staple, suture, grasp, controlling or scaling a camera etc.). Additional features and functionality of the controllers 182 have been described above with reference to FIG. 19, which illustrates one embodiment thereof. Other embodiments of handheld controllers are also possible, including controllers that include keyboards, touchpads, buttons, joysticks, mice, etc.

Figure 22:
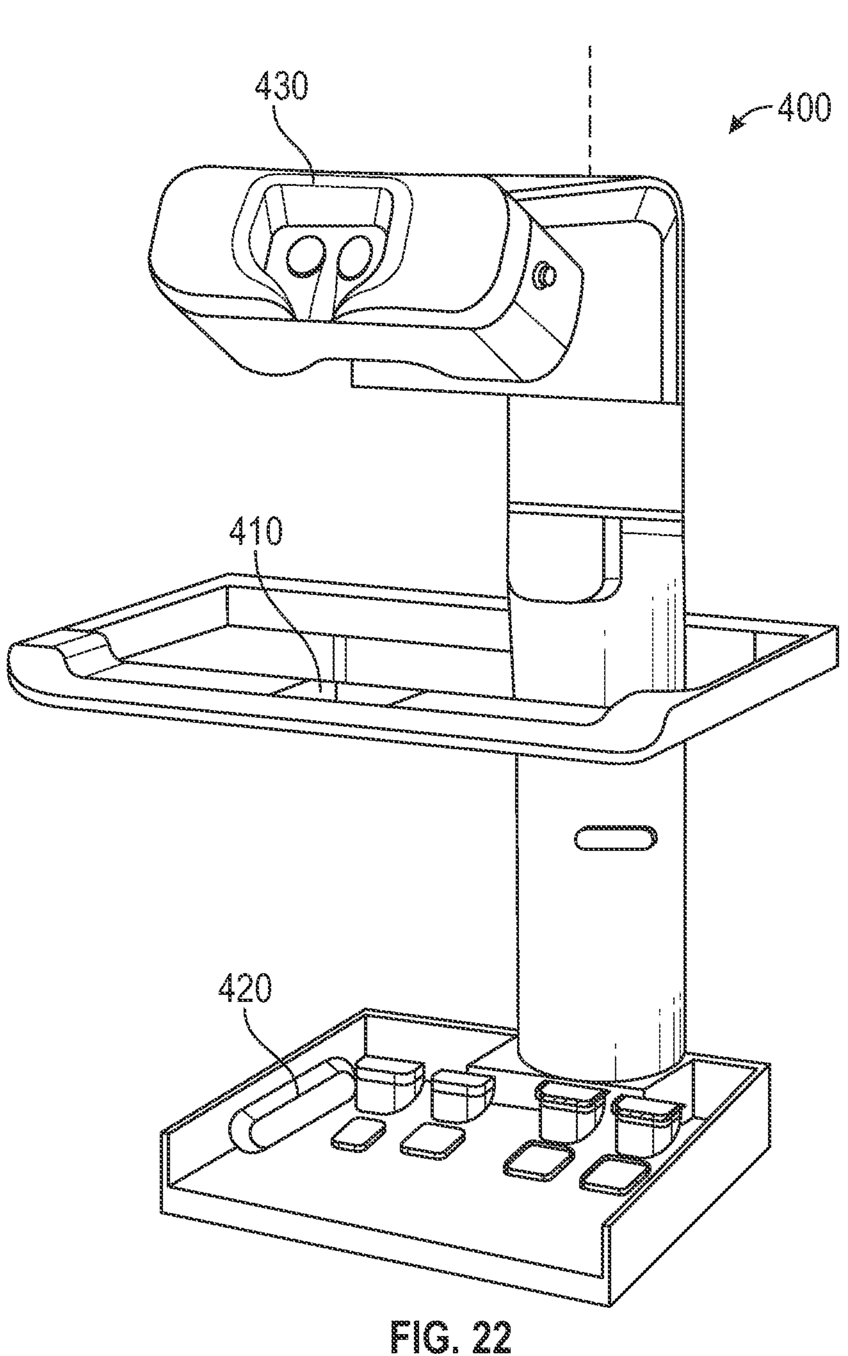
FIG. 22 illustrates an example of a master controller.

FIG. 22 illustrates another example of a master controller 400. The master controller 400 can include a surgeon console viewer 430, a touchpad 410, pedals 420, or gimbals (not shown). The viewer 300 as shown in FIG. 21 may be the surgeon console viewer 430 of the master controller 400. The viewer 300 can include the display configured as described above. In some examples, the telestration mode can be activated by an input on the master controller 400. For example, as described above, the telestration mode can be activated through the viewer 300, which may be a surgeon console viewer 430. The telestration mode can also be activated through the touchpad 410. The telestration mode can be activated by selecting the telestration mode in a menu. The telestration mode can be activated through the master controller 400, such as an activation of a button or a pedal, by taking a distinct action or usual actuation on the master controller 400 (e.g. a double click of the graspers or gimbals). The action of the master controller may be an action or movement of the one or more graspers of the master controller, such as double gripping one of the graspers. In some examples, the user actuation can be movement or contact of a user's finger on a screen, such as on the touchpad 410.

Figure 23:
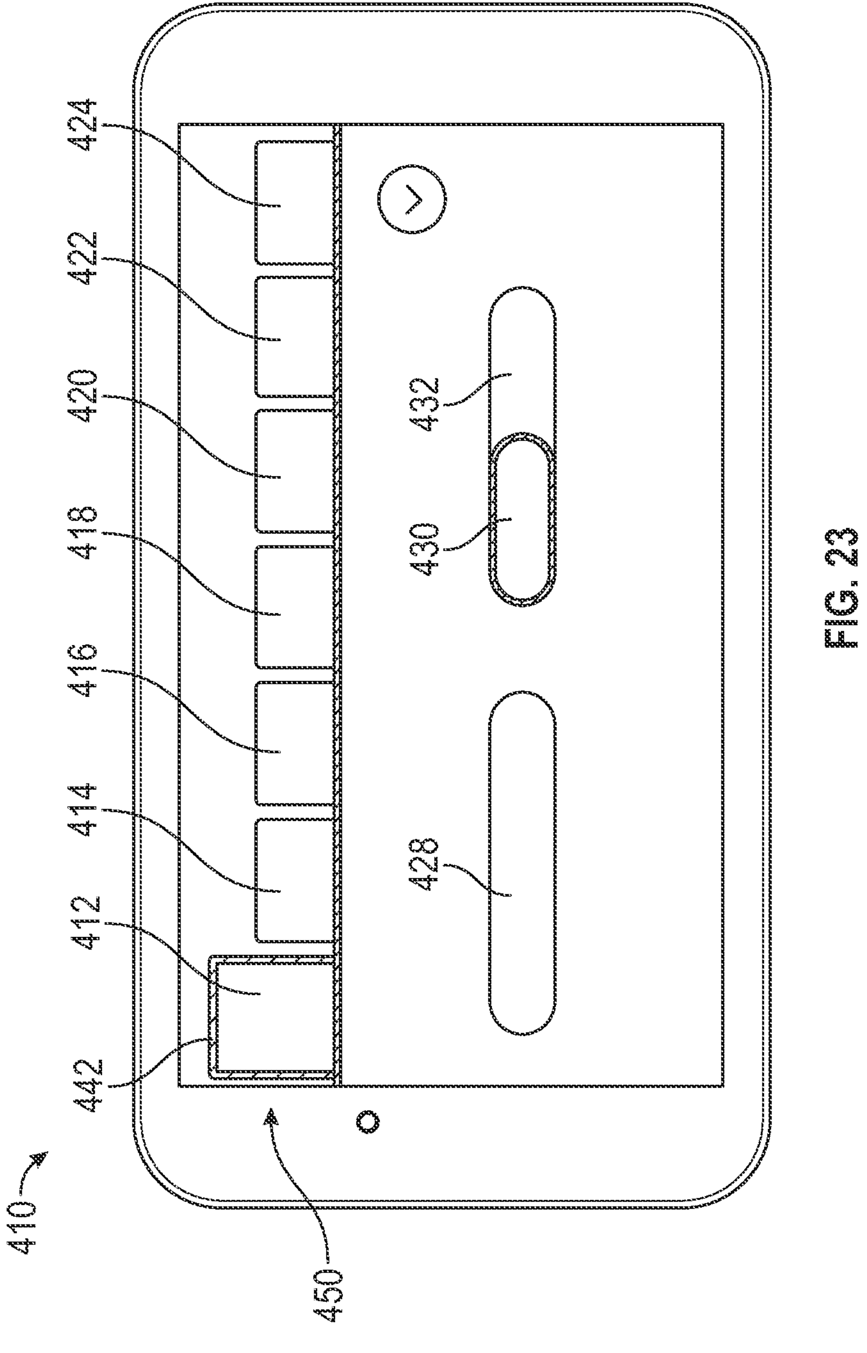
FIG. 23 illustrates an example of a touchpad of a master controller.

FIG. 23 illustrates an example of a touchpad, such as the touchpad 410 of the master controller 400. The touchpad 410 can include a touchpad menu or series of tabs 450 for selection. Each of the series of tabs 450 can be associated with different modes for operation, different instruments, and/or different functions. For example, a series of tabs 200 are shown in FIG. 23, including a first tab 412, a second tab 414, a third tab 416, a fourth tab 418, a fifth tab 420, a sixth tab 422, and a seventh tab 424. The series of tabs 450 can include tabs associated with different modes, such as a teleoperation mode or a telestration mode. The series of tabs 450 can include a tab for the virtual marking tool for telestration, such as the first tab 412. The series of tabs 450 can include tabs associated with other instruments, such as various types of telestration tools (e.g. a marker or highlighter of varying widths or colors) or medical instruments (e.g. graspers, clip or stapler appliers, needle driver, cutter, or sealer), Similar to the series of tabs 200 of the viewer 300 as described above, the series of tabs 450 of the touchpad 410 can be used to switch between modes.

The associated tab of a certain mode or instrument can be bolded, highlighted, enlarged, or otherwise differentiated when a user input is in the associated mode of operation or is coupled to the user input. For example, the first tab 412, when selected, can be shown as the active tab as enlarged and with an indicator 442 positioned around the first tab 412. In some examples, each of the series of tabs 450 may be selectable or clickable, where selecting or clicking a particular tab, the associated mode of operation is activated or when the instrument is coupled to the user input. The menu or series of tab 450 can be positioned anywhere on the touchpad 410. Furthermore, when the particular tab is selected, an associated submenu of items may appear. For example, when the telestration mode is activated, a first button 428 my appear for exchanging the instrument, which may allow the user in the telestration mode to select an instrument for use in the telestration mode, such as a particular marker or highlighter of a particular color or width or a particular medical instrument to be used for telestration. For example, when the telestration mode is activated, a second button 430 may be activated for a particular hand preference of the user (e.g. right hand or left hand). As shown in the illustrated example in FIG. 23, the menu or series of tabs 450 can be positioned on the top side of the touchpad 410.

In some examples, an image of the surgical site could be shown on a user interface touchscreen, such as a viewer 300 or a touchpad 410 of the master controller 400. A surgeon could use a finger, pen, stylus, or other writing utensil on an input of the master controller 400, such as on the touchpad 410, to draw and generate the virtual marker. In some examples, the surgeon can use the gripper or mouse, which can act as an input on the master controller for receiving an input from the user configured to produce or create a virtual marker.

Figure 24:
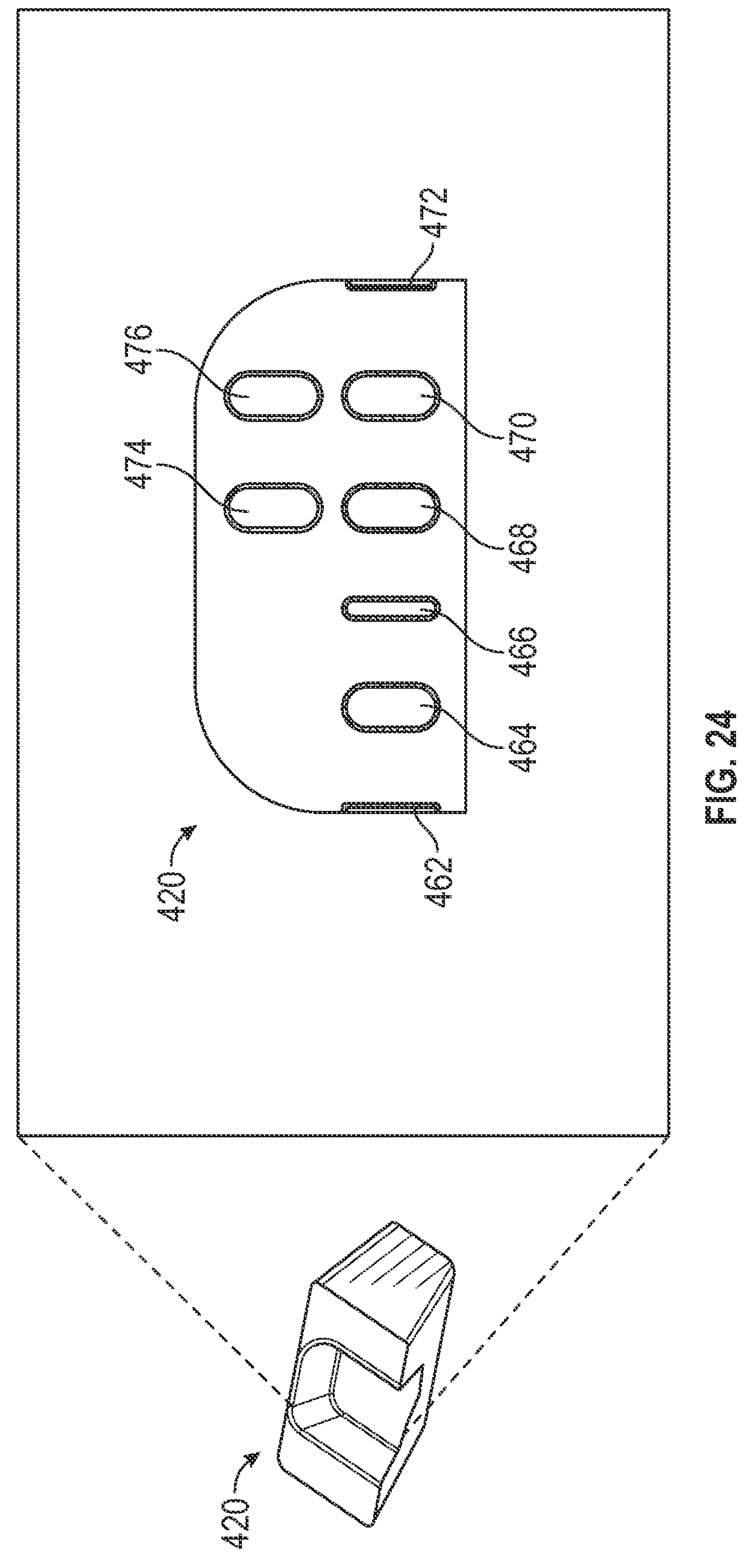
FIG. 24 illustrates an example of a set of pedals of a master controller.

FIG. 24 illustrates an example of pedals, such as the pedals 420 of the master controller 400, which can act as an input on the master controller for receiving an input from the user. The pedals 420 can include a number of pedals for selection. Each of the pedals can be associated with different modes for operation, different instruments, and/or different functions. For example, the pedals 420 can include a first pedal 462, a second pedal 464, a third pedal 466, a fourth pedal 468, a fifth pedal 470, a sixth pedal 472, a seventh pedal 474, and an eight pedal 476. The pedals 420 can be associated with different modes, such as a teleoperation mode or a telestration mode. The pedals 420 can be used to switch between modes and select a menu option, such as the menu 200 shown in the viewer 300 of FIG. 21 or the menu 450 shown in the touchpad 410 of FIG. 23. For example, the first pedal 462 and the sixth pedal 472, which are side pedals positioned on opposite sides, can be used to move through menu options.

Figure 25:
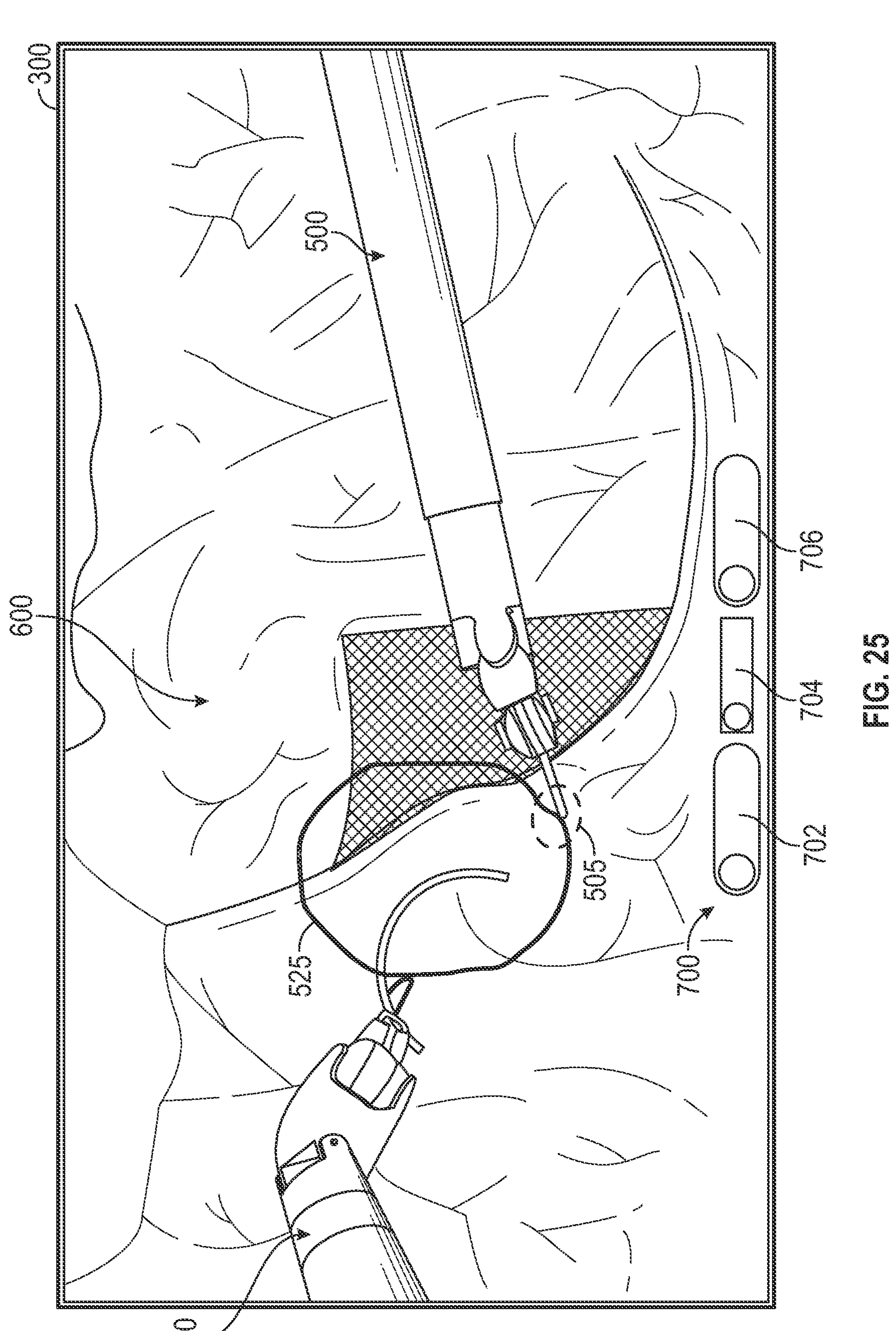
FIG. 25 illustrates an example of a viewer including a virtual marker.

FIG. 25 illustrates exemplary embodiments of a display of a viewer 300 that may include one or more virtual markers. The display of the viewer 300 can also include virtual markers 505, 525 that convey information. The virtual markers can be positioned as visual overlays on an image of a medical instrument and/or an treatment site, which may be a live feed or a representative model or depiction. In the virtual marking or telestration mode, the surgeon can draw virtual objects in 3-D space in a displayed image. This would allow the surgeon to draw on the screen without disrupting the procedure.

In some examples, various medical instruments may be used in telestration, wherein the tip of the physical instrument in the telestration mode may act as a virtual instrument to draw shapes or other virtual symbols as visual overlays in the field of view, Kinematic computation of the instrument position would allow the tip of a physical instrument to act as a virtual instrument. The shapes or objects drawn would be interpreted in software and converted to virtual markers that would be added as a visual overlay on an image. The virtual marker can be added to the image on the laparoscope view displayed in the stereo viewer and/or on auxiliary monitors. This advantageously allows the surgeon to generate a virtual marker without disrupting the procedure.

With the virtual marking mode activated, the surgeon can control and generate virtual marking by using the master controller, which may include grippers or a mouse, which can act as an input for receiving an input from the user configured to produce a virtual marker. The tip of the physical instrument in the telestration mode may act as a virtual instrument to draw shapes or other virtual symbols as visual markers in the field of view. For example, the first medical instrument 500 can be used to generate a first indicator or first virtual marker 505 as a visual overlay and the second medical instrument 520 can be used to generate a second indicator or second virtual marker 525 as a visual overlay. Each medical instrument can generate a distinct indicator or virtual marker, which can be differentiated based on color, pattern, or any other feature. For example, the first virtual marker 505 can be a first color or pattern and the second virtual marker 525 can be a second color or pattern.

The viewer 300 can include a menu or series of tabs 700 that allows the user to select the various medical instruments 500, 520. For example, the first tab 702 can be associated with the first medical instrument 500 and the second tab 704 can be associated with the second medical instrument 520.

Figure 26:
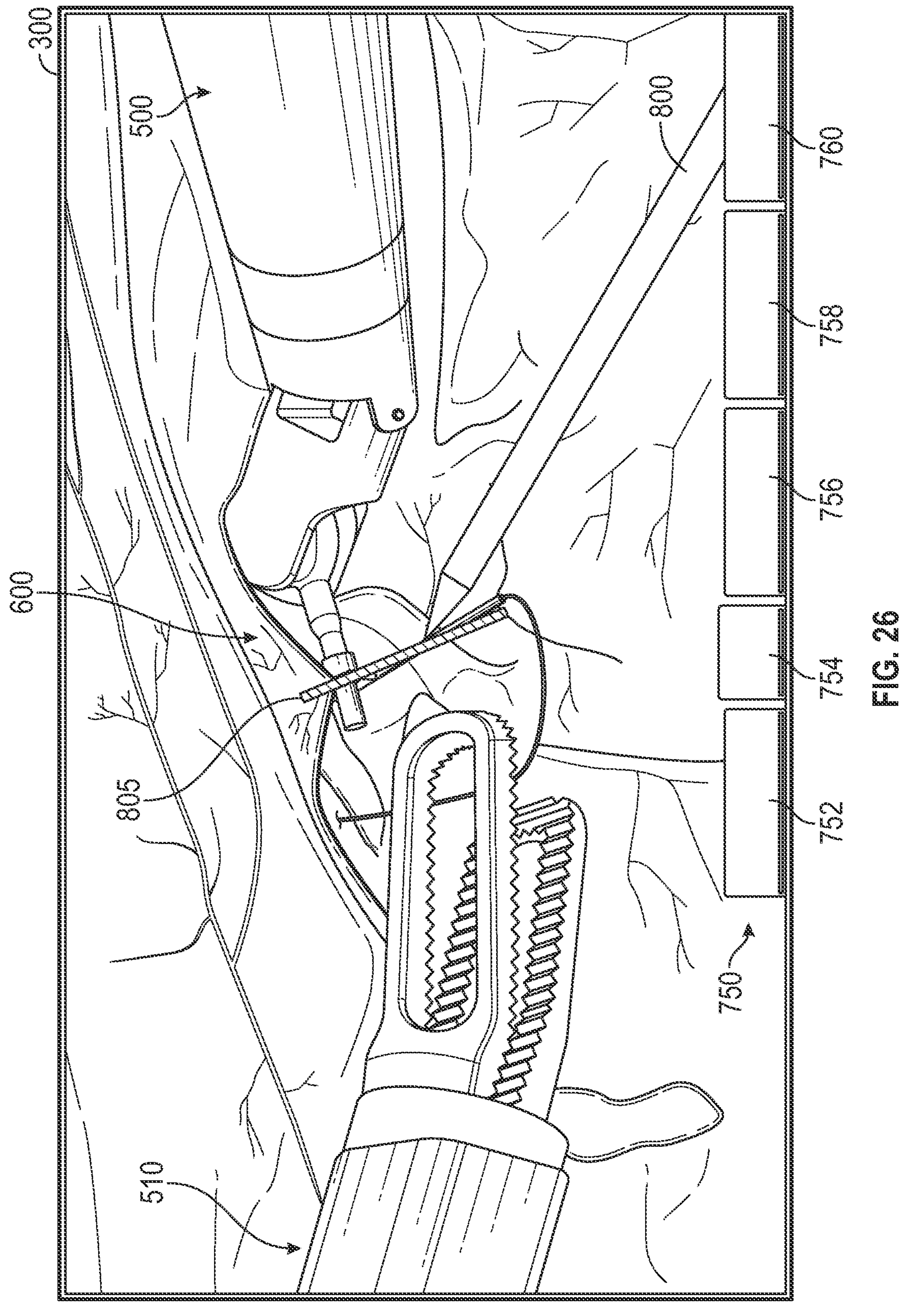
FIG. 26 illustrates an example of a viewer including a virtual marker and a virtual instrument.

FIG. 26 illustrates exemplary embodiments of a display of a viewer 300 that may include one or more virtual markers. The viewer 300 can also include a virtual marker 805 that is positioned as a visual overlay to convey information. With the virtual marking mode activated, the surgeon can control and generate virtual marking.

With the virtual marking mode activated, the surgeon can control and generate one or more virtual markers by using the master controller, which may include grippers, a mouse, a touchscreen, or any other input device. In some examples, a virtual instrument 800 can be used to generate virtual markers as visual overlays in the field of view. The virtual instrument 800 can be shown as a visual overlay in the viewer 300. In some examples, various virtual instruments of different types (e.g. colors, widths, boldness, patterns) can be used. The shapes drawn would be interpreted in software and converted to virtual objects, such as lines or 3D objects, that would be added as a visual m on the viewer.

The viewer 300 can include a menu or series of tabs 750 that allows the user to select the various instruments, including one or more virtual instruments. For example, the first tab 752 can be associated with the virtual instrument 800, the second tab 704 can be associated with the first medical instrument 500, and the third tab 756 can be associated with a fourth medical instrument 510.

Figure 27:
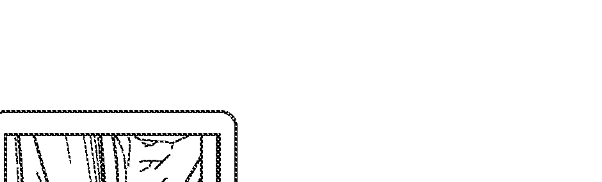
FIG. 27 illustrates an example of a master controller and a tower console.
Figure 27:
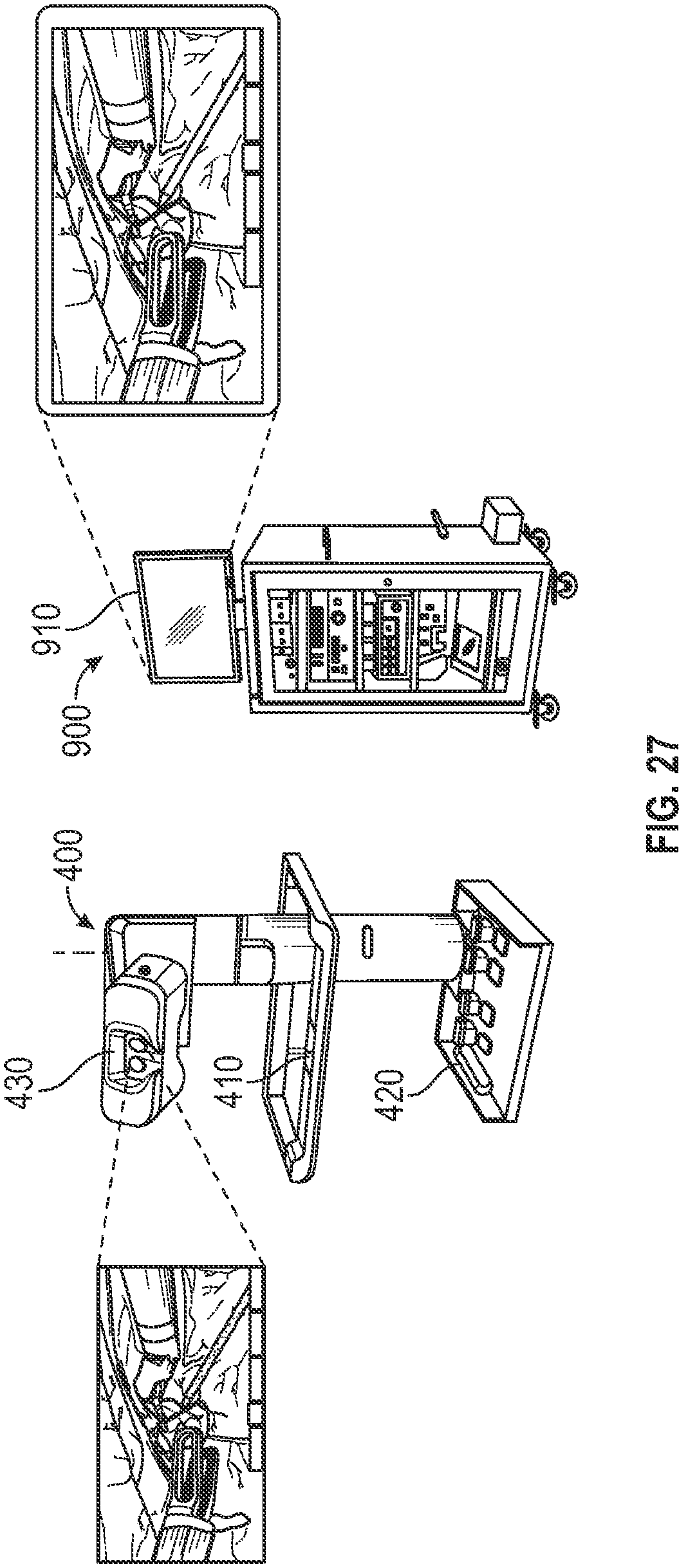

FIG. 27 illustrates a system showing the master controller 400 and a tower 900 with a tower console 910. As previously described, the surgeon may generate a virtual marker as a visual overlay on an image and view the visual overlay on a first display, such as on a display of the surgeon console viewer 430. Once the surgeon generates the virtual marker as a visual overlay, the virtual marker on the image can be communicated by displaying the virtual marker in a secondary location on a second display, such as on a display of the tower console 910 of the tower 900. In other examples, the virtual marker can also be displayed in various other locations, such as on a display of a stereoscopic viewer of the surgeon console or an external monitor (e.g. a video output). In some examples, these images can be recorded.

In some examples, a staff or user is not only able to see the virtual marker displayed on the secondary location but can also interact with the virtual marker. In some examples, a staff or other user, such as a nurse or bedside operating room staff, can similarly generate a virtual marker at a secondary location that can be communicated to the surgeon at the surgeon console or to yet another user. In some examples, the second user can use a touchscreen in the tower console 910 or an input of the tower 900 to generate or manipulate a virtual marker.

In some examples, the virtual marker generated can remain in the surgeon's view even when the field of view of the anatomy changes. In other words, the virtual marker can be fixed with respect to the screen or to the robot.

Figure 28A:
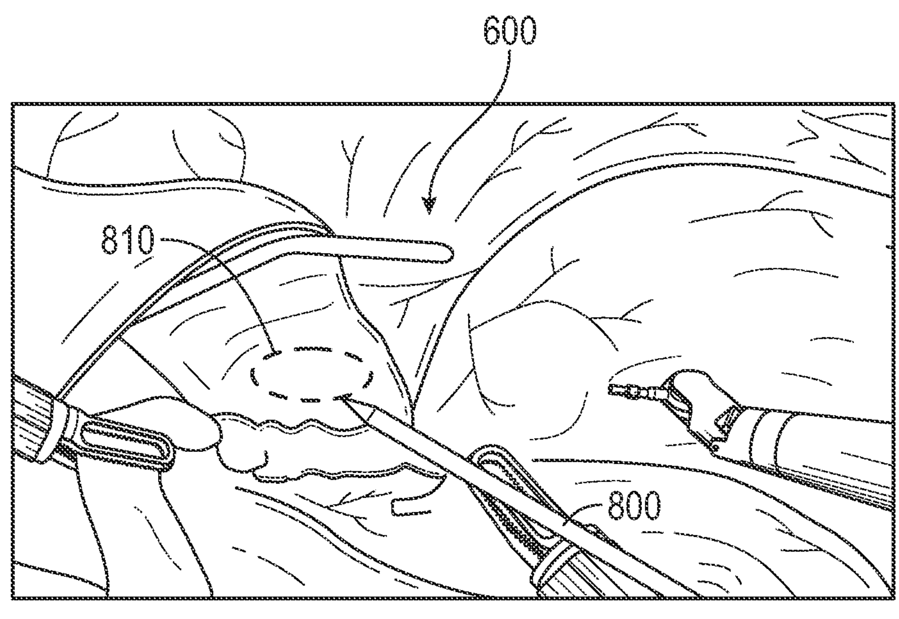
FIG. 28A illustrates a virtual instrument and generated virtual marker for marking an area within the treatment site.

In some examples, the virtual marker generated can be fixed to the anatomy, such as to a point in the representation of the surgical site within the anatomy. FIG. 28A illustrates a virtual instrument 800 and generated virtual marker 810 and virtual instrument 800 for marking an area within the treatment site 600. The virtual marker 810 can be located in 3-D space such that it is registered or fixed in plate with respect to the anatomy. As the virtual marker 810 can be located in 3-D space, this means that the virtual marker 810 can go in and out of view, even when the camera is moved and the field of view changes.

Figure 28B:
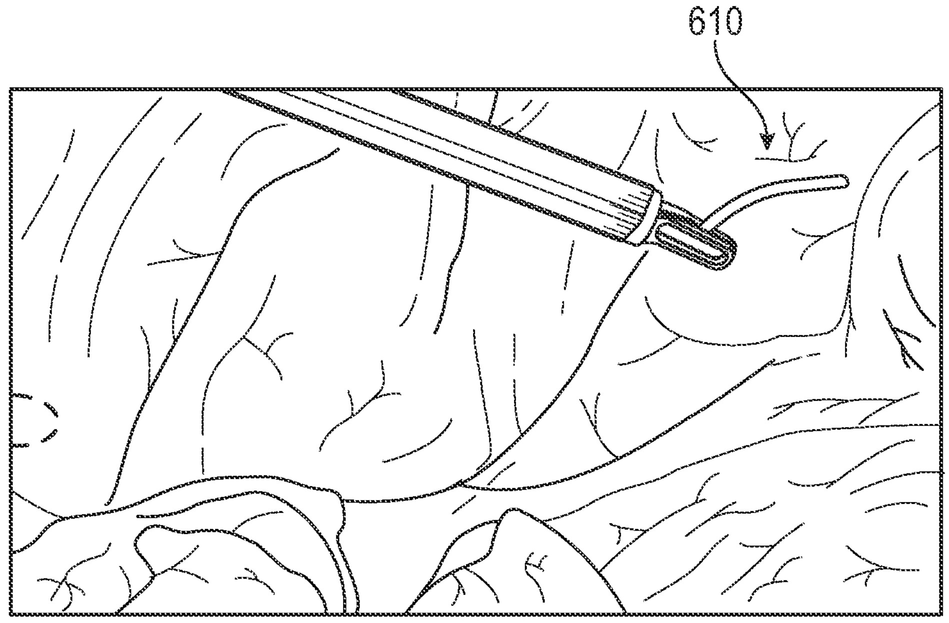
FIG. 28B illustrates a change in the view of to a different treatment site.

FIG. 28B illustrates a change in the view of to a different treatment site 610 such that the virtual marker 810 is out of view and not visible. For example, the field of view can be changed to perform another segment of the procedure or observe another area within the anatomy. The virtual marker 810 can remain in position within the anatomy in the prior treatment site 600.

Figure 28C:
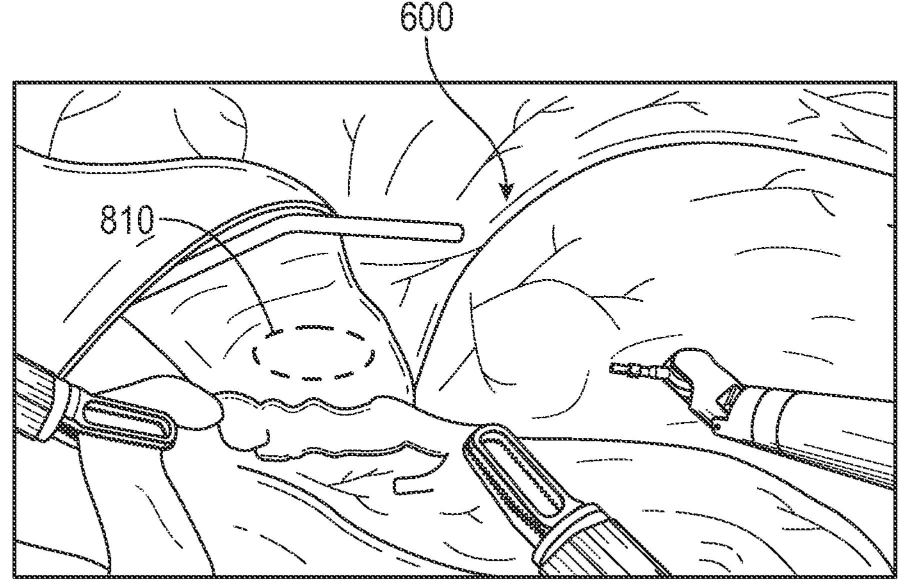
FIG. 28C illustrates a return to the previous field of view of the treatment site showing the generated virtual marker positioned in the treatment site.

FIG. 28C illustrates a return to the previous field of view of the treatment site 600 showing the generated virtual marker 810 positioned in the prior treatment site 600, In some examples, the virtual marker 810 can be fixed to an anatomy such that it changes as the field of view changes, even if it remains within the field of view. For example, the virtual marker can be fixed to a certain anatomy (e.g. a lesion or cancerous area), If the change of view shifts such that the certain anatomy is positioned farther away.

The place holding of the virtual markers can be advantageous in that the virtual marker 810 can remain on a particular anatomy that was highlighted, even when the camera has moved or shifted. The virtual markers generated during telestration could persist in 3-D space and stay in position on the anatomy even as the camera moves. This can advantageously allow the surgeon or user to mark features and maintain the virtual marker, even when the features are out of the current field of view. A surgeon who is surveying an area of anatomy and notices an area of interest (e.g., an anomaly), can then highlight or circle the area using telestration and generating a virtual marker, and can revisit the area at a later time. In another example, a surgeon can desire to perform a procedure in a different area (e.g., remove a suture from another area) and then the surgeon will be able to return to the location of telestration. The generated virtual marker being held in place can also be used to allow a surgeon to orient the field of view as desired as a point of reference. For example, the surgeon may use the virtual marker to recall or retrieve a prior position and orientation.

Figure 29:
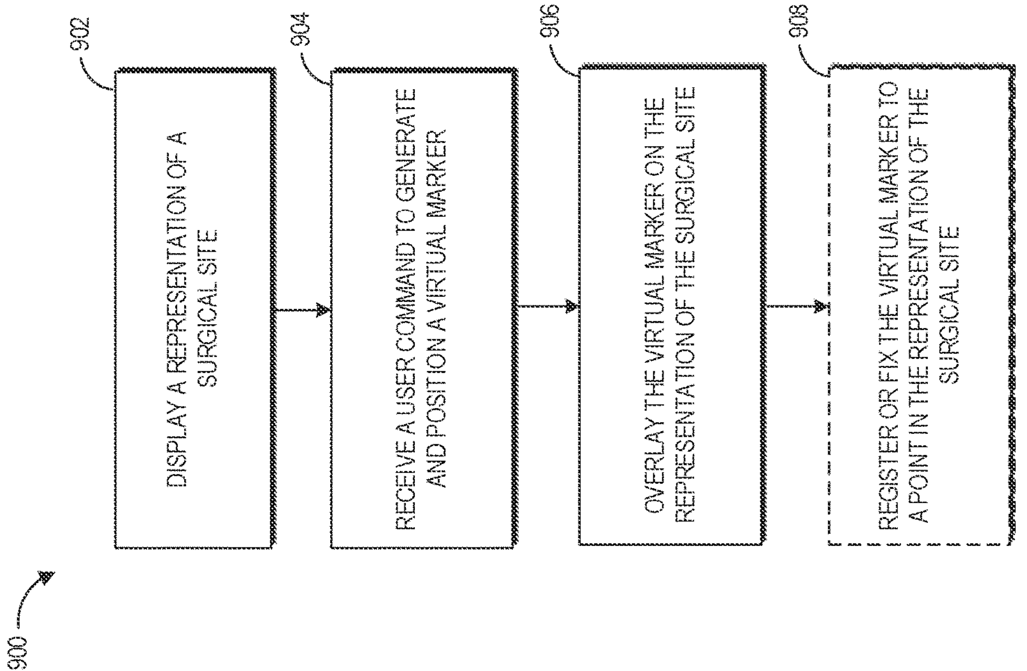
FIG. 29 is a flow chart depicting an example method for implementing virtual indicators.

FIG. 29 illustrates an example method 900 for implementing virtual markers in a robotic medical system as described herein. The method 900 begins at block 402, which includes displaying a representation of a surgical site. This representation of the surgical site can display a representation of the surgical site when operating the robotic medical system.

At block 904, the method 900 includes receiving a user command to generate and position a virtual marker. As described above, the user command can be given through user actuation of a master controller. For example, the user actuation can include actuation, movement, or performing an action of one or more graspers, a button, a foot pedal, or a screen. For example, the user actuation can include movement of a user's finger on a screen. For example, the user actuation can include double gripping of one or more graspers. As also described above, the user command can be initiated by activating a virtual marking mode. The virtual marking mode can be activated by selecting the virtual marking mode in a menu.

At block 906, the method 900 includes overlaying the virtual marker on the representation of the surgical site. As described above, the virtual markers can be visually displayed on a viewer (e.g., as shown in FIGS. 25-26). As described herein, the virtual markers can be overlaid on the representation of the surgical site, displayed on a display of one more viewers, such as a display of a master controller, a viewing screen of a tower, or a screen. The virtual markers as visual overlays on the representation of the surgical site can be communicated to at least two users in at least two different locations. In some examples, the method 900 can optionally include registering or fixing, the virtual marker to a point in the representation of the surgical site at block 908. As described herein, registering or fixing the virtual marker to a fixed point in the representation of the surgical site can allow the virtual marker remains fixed to the point in the representation of the surgical site when the camera view changes.

3. Implementing Systems and Terminology

Implementations disclosed herein provide systems, methods and apparatus associated with virtual markers configured for use with robotic medical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

Any phrases referencing specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A surgical system comprising:

a master controller for controlling one or more surgical tools; and an input on the master controller configured to change the master controller from a first mode into a second mode, wherein the first mode comprises a teleoperation mode and the second mode comprises a virtual marking mode, wherein, in the teleoperation mode, the master controller is configured to move or actuate the one or more surgical tools, the one or more surgical tools being operable to manipulate tissue, and, in the virtual marking mode, the master controller is configured to generate a virtual marker on one or more displays, the virtual marker being generated via a user manipulation of at least one of the one or more surgical tools.

2. A surgical system comprising:

a master controller for controlling one or more surgical tools;

a viewer on the master controller configured to display a representation of a surgical site;

a screen separate from the master controller configured to display the representation of the surgical site; and an input on the master controller configured to change the master controller from a teleoperation mode into a virtual marking mode, wherein, in the teleoperation mode, the master controller is configured to move or actuate the one or more surgical tools, and, in the virtual marking mode, the master controller is configured to generate a virtual marker overlayed on the representation of the surgical site in the screen separate from the master controller, wherein in the virtual marking mode, the screen separate from the master controller is operable to one or both of (i) modify the virtual marker generated at the master controller and overlayed on the representation of the surgical site to thereby provide a modified virtual marker, or (ii) generate another virtual marker overlayed on the representation of the surgical site to thereby provide a generated other virtual marker, wherein the viewer on the master controller is further configured to display one or both of (i) the modified virtual marker, or (ii) the generated other virtual marker.

3. The surgical system of claim 2, wherein the input comprises an action of one or more graspers of the master controller.

4. The surgical system of claim 3, wherein the action comprises a double gripping of at least one of the graspers of the master controller.

5. The surgical system of claim 1, wherein, in the virtual marking mode, a user at the master controller is capable of communicating the virtual marker to other staff at a patient site separate from the master controller.

6. The surgical system of claim 2, wherein the virtual marker comprises a hand-drawn overlay positioned over a representation of a surgical site.

7. The surgical system of claim 2, wherein the screen separate from the master controller comprises a screen of a tower.

8. The surgical system of claim 2, wherein, in the teleoperation mode, a viewer of the master controller is configured to display an image captured by a camera controlled by the master controller.

9. The surgical system of claim 1, wherein, in the virtual marking mode, a screen of a tower separate from the master controller is configured to display the virtual marker, and the tower is configured to generate or manipulate a virtual marker displayed on a viewer of the master controller.

10. The surgical system of claim 7, wherein the screen of the tower is a touchscreen configured to manipulate the virtual marker generated by the master controller.

11. The surgical system of claim 2, wherein, in the virtual marking mode, the master controller is configured for two-way communication between users.

12. The surgical system of claim 2, wherein, in the teleoperation mode, one or more graspers of the master controller are configured to move or actuate the one or more surgical tools, and, in the virtual marking mode, the one or more graspers are configured to generate or position the virtual marker.

13. The surgical system of claim 2, wherein, in the teleoperation mode, one or more graspers of the master controller are configured to move or actuate the one or more surgical tools, and, in the virtual marking mode, a touchpad of the master controller is configured to generate or draw the virtual marker.

14. The surgical system of claim 2, wherein the input comprises a button on the master controller.

15. A method of communication during surgery comprising:

displaying, at a viewer of a master controller, a representation of a surgical site;

displaying, at a screen separate from the master controller, the representation of the surgical site;

controlling, in a teleoperation mode, one or more surgical tools in response to user input at the master controller;

changing the master controller from the teleoperation mode into a virtual marking mode in response to user input at the master controller;

generating, in the virtual marking mode, a virtual marker overlayed on the representation of the surgical site at the screen separate from the master controller in response to user input at the master controller, the virtual marker being defined by a user by manipulating the user input at the master controller such that the virtual marker is a user-defined virtual marker, the user-defined virtual marker being defined in relation to an anatomical structure at the surgical site to thereby associate the user-defined virtual marker with the anatomical structure; and fixing the user-defined virtual marker to a point in the representation of the surgical site, the point positioned at the anatomical structure associated with the user-defined virtual marker, wherein the user-defined virtual marker remains fixed to the point in the representation of the surgical site when a camera view changes.

16. The method of claim 15, further comprising displaying the user-defined virtual marker on the representation of the surgical site on the viewer of the master controller.

17. The method of claim 15, further comprising communicating the user-defined virtual marker on the representation of the surgical site to at least two users in two different locations.

18. The method of claim 15, wherein the controlling of the one or more surgical tools is based on user actuation of one or more graspers of the master controller, and wherein the generating of the user-defined virtual marker is based on user actuation of the one or more graspers of the master controller.

19. The method of claim 15, wherein the controlling of the one or more surgical tools is based on user actuation of one or more graspers of the master controller, and wherein the generating of the user-defined virtual marker is based on movement of a finger of the user on a touchscreen of the master controller.

* * * * *